(12) United States Patent  (10) Patent No.: US 8,653,082 B2
Nir et al.  (45) Date of Patent: Feb. 18, 2014

(54) 6-PHENYL-2-[((PIPERIDIN-4-YLMETHYL)-PIPERAZIN-1YL) OR PIPERAZIN 1-YLMETHYL)-PIPERIDIN-1-YL)]-IMIDAZO[2,1-B][1,3,4]THIADIAZOLE DERIVATIVES AND THEIR USE

(75) Inventors: Uri Nir, Moshav Gamzo (IL); Sally Shpungin, Ramat-Gan (IL); Etai Yaffe, Oranit (IL); Moshe Cohen, Kfar Saba (IL)

(73) Assignee: Urifer Ltd., Raanana (IL)

( * ) Notice: Subject to any disclaimer, the term of this patent is extended or adjusted under 35 U.S.C. 154(b) by 119 days.

(21) Appl. No.: 13/203,172

(22) PCT Filed: Feb. 25, 2010

(86) PCT No.: PCT/IL2010/000164
§ 371 (c)(1),
(2), (4) Date: Aug. 24, 2011

(87) PCT Pub. No.: WO2010/097798
PCT Pub. Date: Sep. 2, 2010

(65) Prior Publication Data
US 2011/0306619 A1  Dec. 15, 2011

Related U.S. Application Data

(60) Provisional application No. 61/202,402, filed on Feb. 25, 2009.

(51) Int. Cl.
*A61K 31/497* (2006.01)
*C07D 417/04* (2006.01)

(52) U.S. Cl.
USPC ........................... 514/253.1; 544/364

(58) Field of Classification Search
USPC ........................... 514/253.1; 544/364
See application file for complete search history.

(56) References Cited

U.S. PATENT DOCUMENTS

2005/0063973 A1  3/2005  Nir

FOREIGN PATENT DOCUMENTS

WO  2009019708 A2  2/2009

OTHER PUBLICATIONS

Cancer Drug Design and Discovery, Neidle, Stephen,ed. (Elsevier/Academic Press), pp. 427-431 (2008).*

(Continued)

*Primary Examiner* — James O Wilson
*Assistant Examiner* — Ebenezer O Sackey
(74) *Attorney, Agent, or Firm* — Browdy and Neimark, PLLC

(57) ABSTRACT

Heterocyclic compounds of formula (I), (II), (III) or a pharmaceutically acceptable salt thereof:

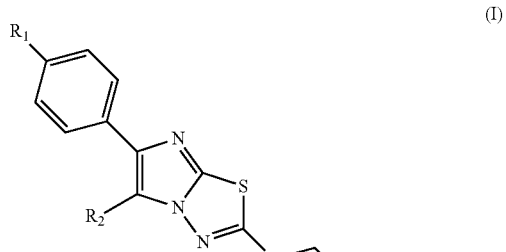

(I)

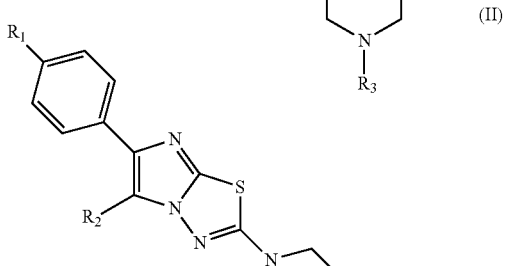

(II)

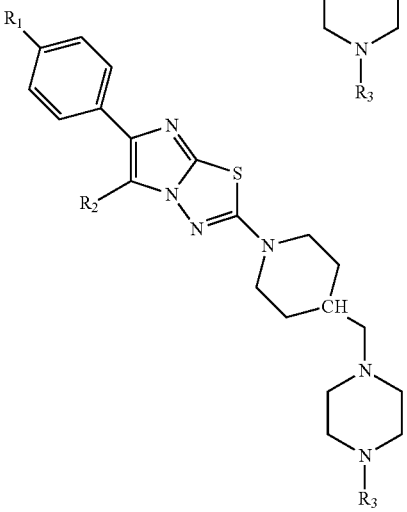

wherein $R_1$, $R_2$ and $R_3$ are each independently selected from hydrogen, halogen, $C_{1-6}$alkyl, $C_{2-6}$alkenyl, N—$(C_{1-6}$alkyl$)_2$, and N—$(C_{2-6}$alkenyl$)_2$, the $C_{1-6}$alkyl and $C_{2-6}$alkenyl being straight or branched; and $Y_1$ and $Y_2$ are selected from N and CH where one of $Y_1$ and $Y_2$ is N and the other is CH, are provided. Also provided are the synthesis of and pharmaceutical compositions including these compounds. These compounds and pharmaceutical compositions thereof can be used for the treatment of disorders, and in particular, cancer.

11 Claims, 10 Drawing Sheets

(56) References Cited

OTHER PUBLICATIONS

Allard et al., "Links between Fer tyrosine kinase expression levels and prostate cell proliferation" Mol. Cell. Endocrinol., 159, 63-77 (2000).

Berridge et al., "Tetrazolium dyes as tools in cell biology: new insights into their cellular reduction" Biotechnol. Annu. Rev. 11:127-152 (2005).

Craig et al., "Fer Kinase Is Required for Sustained p38 Kinase Activation and Maximal Chemotaxis of Activated Mast Cells" Mol. Cell. Biol., 22:6363-6374 (2002).

Craig et al., "Mice Devoid of Fer Protein-Tyrosine Kinase Activity Are Viable and Fertile but Display Reduced Cortactin Phosphorylation" Mol. Cell. Biol., 21:603-613 (2001).

Greer P., "Closing in on the Biological Functions of FPS/FES and FER" Nat. Rev. Mol. Cell Biol., 3:278-289 (2002).

Hao et al., "Isolation and Sequence Analysis of a Novel Human Tyrosine Kinase Gene" Mol. Cell. Biol., 9:1587-1593 (1989).

Kim et al., "Growth Factor-dependent Phosphorylation of the Actin-binding Protein Cortactin Is Mediated by the Cytoplasmic Tyrosine Kinase FER*" Biol. Chem., 273:23542-23548 (1998).

Orlovsky et al., "N-Terminal Sequences Direct the Autophosphorylation States of the FER Tyrosine Kinases in Vivo†" Biochemistry, 39:11084-11091 (2000).

Penhallow et al., "Temporal Activation of Nontransmembrane Protein-tyrosine Kinases following Mast Cell FceRI Engagement*"Biol. Chem. 270:23362-23365 (1995).

Pasder et al., "Downregulation of Fer induces PP1 activation and cell-cycle arrest in malignant cells" Oncogene 25:4194-4206 (2006).

Pasder et al.,"FER as a novel target for cancer therapy" Drugs of the Future, 32:61-70 (2007).

International Search Report mailed Jul. 7, 2010 for PCT/IL2010/00016.

\* cited by examiner

6-PHENYL-2-[((PIPERIDIN-4-YLMETHYL)-PIPERAZIN-1YL) OR PIPERAZIN 1-YLMETHYL)-PIPERIDIN-1-YL)]-IMIDAZO[2,1-B][1,3,4]THIADIAZOLE DERIVATIVES AND THEIR USE

This is a National Phase Application filed under 35 U.S.C. §371 as a national stage of PCT/IL2010/000164, filed on Feb. 25, 2010, an application claiming the benefit under 35 U.S.C. §119(e) of U.S. Provisional Application No. 61/202,402, filed on Feb. 25, 2009, the content of each of which is hereby incorporated by reference in its entirety.

FIELD OF THE INVENTION

This invention relates to imidazo[2,1-b][1,3,4]thiadiazole derivatives, processes for their manufacture and their use in medicaments.

BACKGROUND OF THE INVENTION

The following references are considered to be relevant for an understanding of the invention.

REFERENCES

Allard P, Zoubeidi A, Nguyen L T, Tessier S, Tanguay S, Chevrette M, Aprikian A and Chevalier S. (2000). *Mol. Cell. Endocrinol.*, 159, 63-77.
Berridge, M. V., Herst, P. M., and Tan, A. S. (2005). Tetrazolium dyes as tools in cell biology: new insights into their cellular reduction. Biotechnol. Annu. Rev. 11, 127-152]
Craig A W and Greer P A. (2002). *Mol. Cell. Biol.*, 22, 6363-6374.
Craig A W, Zirngibl R, Williams K, Cole L A and Greer P A. (2001). *Mol. Cell. Biol.*, 21, 603-613.
Greer P. (2002). *Nat. Rev. Mol. Cell Biol.*, 3, 278-289.
Hao Q-L, Heisterkamp N and Groffen J. (1989). *Mol. Cell. Biol.*, 9, 1587-1593.
Kim L and Wong T W. (1998). *J. Biol. Chem.*, 273, 23542-23548.
Orlovsky K, Ben-Dor I, Priel-Halachmi S, Malovany H and Nir U. (2000). *Biochemistry*, 39, 11084-11091.
Penhallow R C, Class K, Sonoda H, Bolen J B and Rowley R B. (1995). *J. Biol. Chem.*, 270, 23362-23365.
Pasder, O., Shpungin, S., Salem, Y., Makovsky, A., Vilchick, S., Michaeli, S., Malovani, H. and Nir, U. (2006) *Oncogene*, 25, 4194-4206.
Pasder, O., Salem, Y., Yaffe, E., Shpungin, S. and Nir, U. (2007) *Drugs of the Future*, 32, 61-70.

Fer is an intracellular tyrosine kinase that resides in both the cytoplasm and nucleus of mammalian cells and is activated by growth factors such as EGF and PDGF in fibroblastic cells (Kim and Wong, 1998), and by occupation of the Fcγ receptor in mast cells (Penhallow et al., 1995). Although present in a wide variety of tissues and cells, the functional role of Fer has been elucidated mainly in cells which carry out innate immune responses (Craig and Greer, 2002; Greer, 2002). Mice devoid of an active Fer develop normally and the proliferation of fibroblasts derived from these mice is not impaired in vitro (Craig et al., 2001).

Fer was detected in all human malignant cell lines analyzed (Hao et al., 1989; Orlovsky et al., 2000) and its levels in malignant prostate tumors are significantly higher then those detected in benign prostate tumors (Allard et al., 2000). Furthermore, down-regulation of Fer impaired the proliferation of prostate and breast carcinoma cells (Pasder et al.,2006) and abolished the ability of prostate carcinoma PC3 cells to form colonies in soft agar (Allard et al., 2000). U.S. patent application Ser. No. 10/486,101 having Publication Number 20050063973 discloses short interfering RNA (siRNA) molecules directed to sequences of the fer gene. These siRNA molecules were found to inhibit the growth of PC3 cells and to arrest tumor growth in an animal model (Pasder et al., 2007).

SUMMARY OF THE INVENTION

In its first aspect the present invention relates to a compound of formula (I) or pharmaceutical salts thereof:

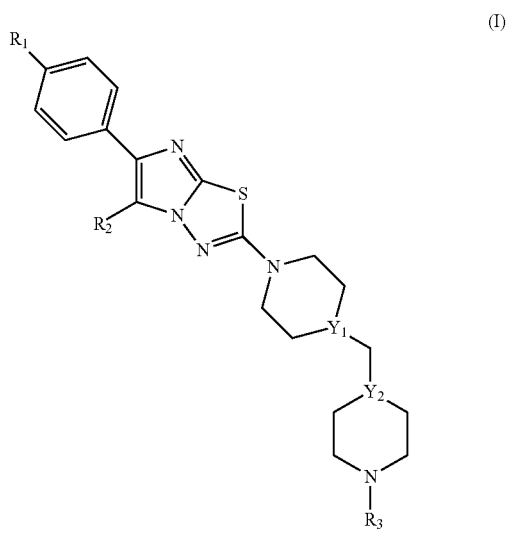

(I)

wherein $R_1$, $R_2$ and $R_3$ are each independently selected from hydrogen, halogen, $C_{1-6}$ alkyl, $C_{2-6}$ alkenyl, N—$C_{1-6}$ alkyl, N—$C_{2-6}$ alkenyl, the $C_{1-6}$ alkyl and $C_{2-6}$ alkenyl being straight or branched; and $Y_1$ and $Y_2$ are selected from N and CH where one of $Y_1$ and $Y_2$ is N and the other is CH.

The invention is further directed to compounds of formulae (II) and (III) and their acceptable pharmaceutical salts.

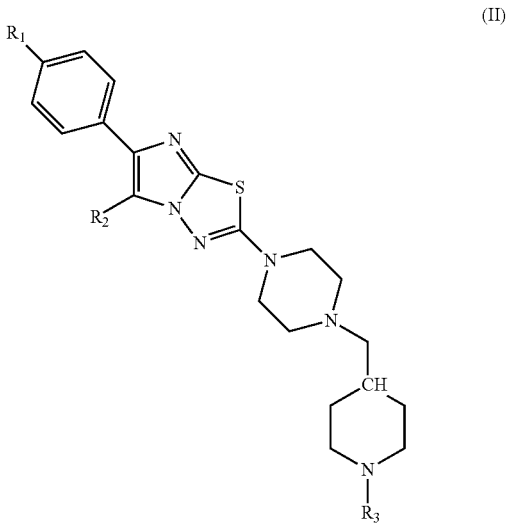

(II)

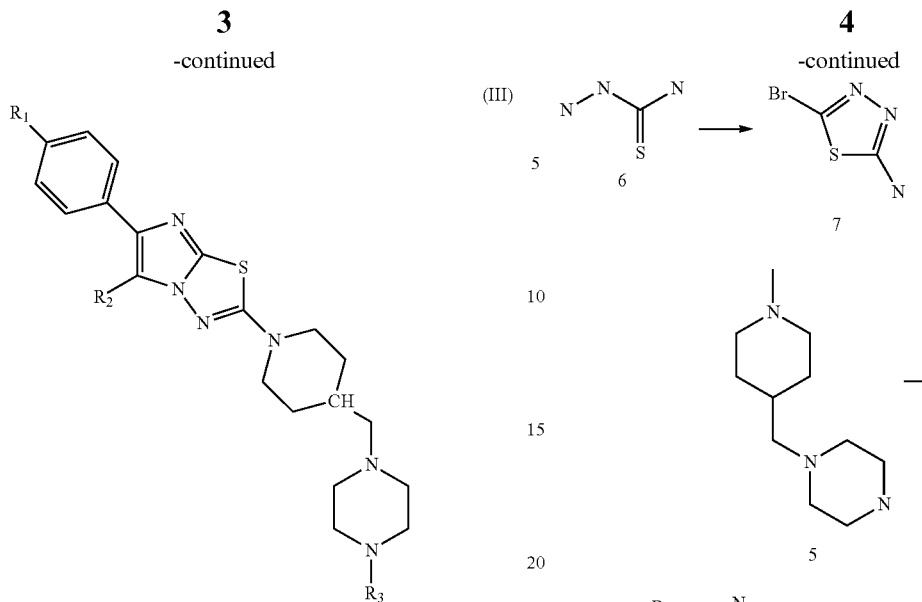

wherein $R_1$, $R_2$ and $R_3$ are each independently selected from hydrogen, halogen, $C_{1-6}$ alkyl, $C_{2-6}$ alkenyl, N—$C_{1-6}$ alkyl, N—$C_{2-6}$ alkenyl the $C_{1-6}$ alkyl and $C_{2-6}$ alkenyl being straight or branched.

The invention is further directed to compounds of formulae (II) and (III) where $R_1$ is a methyl, ethyl, propyl, isopropyl, N-isopropyl, butyl, sec-butyl, tert-butyl, N-butyl, N-sec-butyl, N-tert-butyl, F, Cl, Br, or I; $R_2$ is hydrogen, methyl, ethyl, propyl, isopropyl, or butyl; and $R_3$ is hydrogen, methyl, ethyl, propyl, isopropyl, butyl.

The invention is further directed to processes for the manufacture of compounds of formulae (II) and (III).

A compound of formula (II) is prepared according to the following scheme:

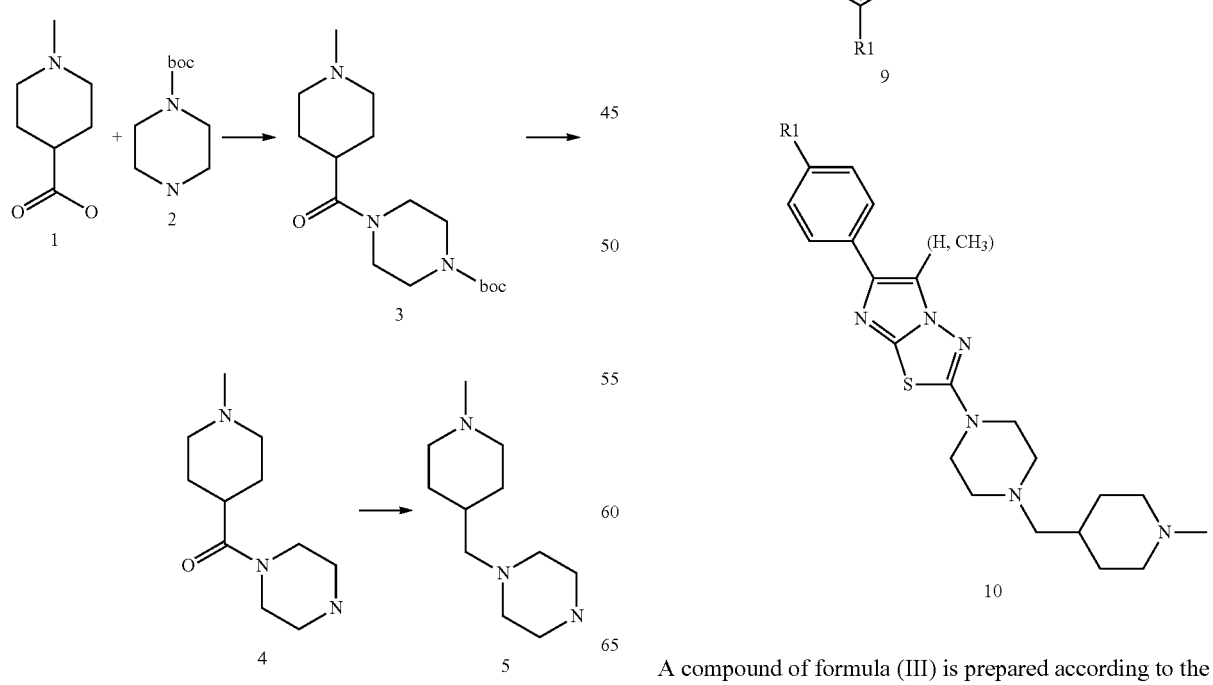

A compound of formula (III) is prepared according to the following scheme:

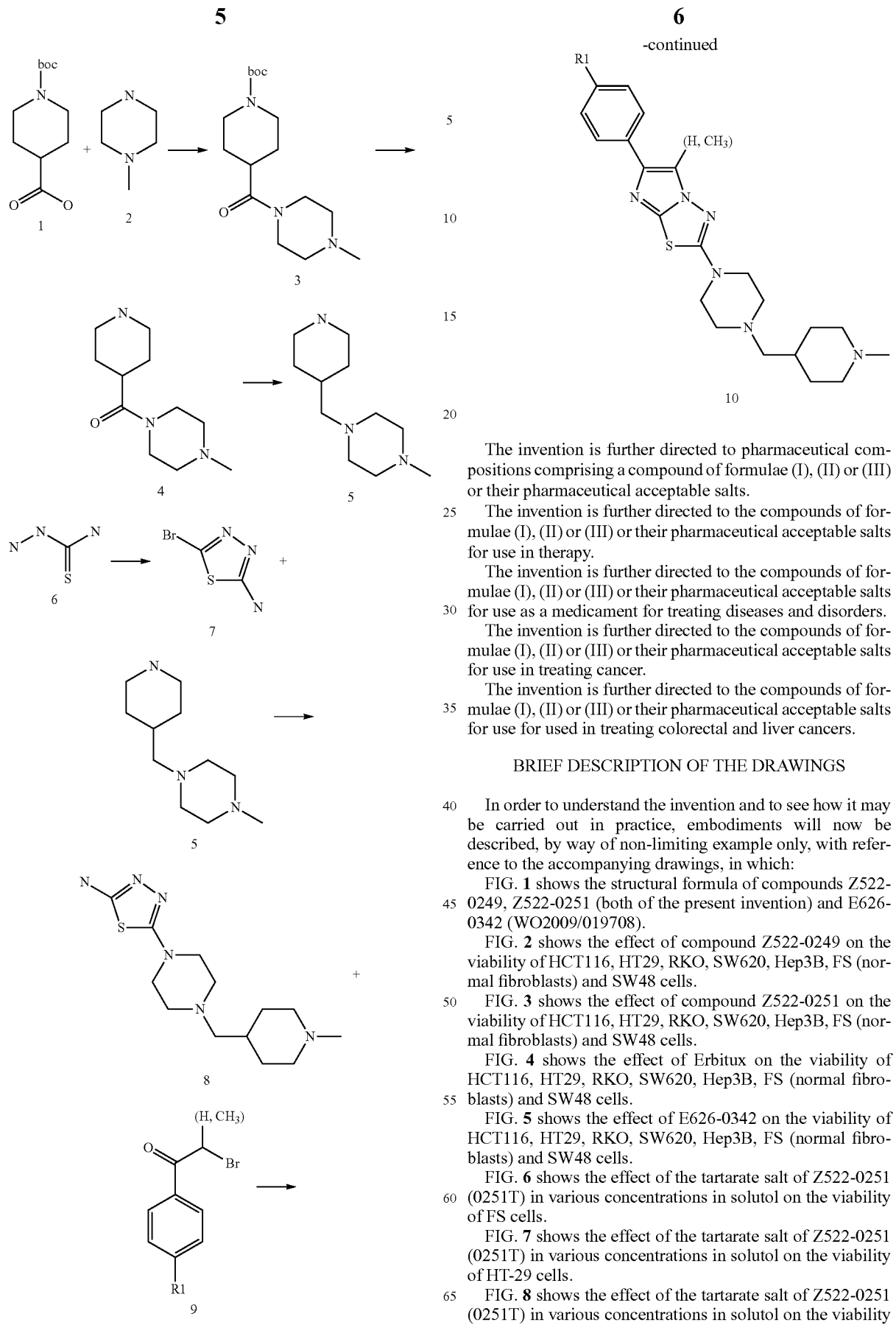

The invention is further directed to pharmaceutical compositions comprising a compound of formulae (I), (II) or (III) or their pharmaceutical acceptable salts.

The invention is further directed to the compounds of formulae (I), (II) or (III) or their pharmaceutical acceptable salts for use in therapy.

The invention is further directed to the compounds of formulae (I), (II) or (III) or their pharmaceutical acceptable salts for use as a medicament for treating diseases and disorders.

The invention is further directed to the compounds of formulae (I), (II) or (III) or their pharmaceutical acceptable salts for use in treating cancer.

The invention is further directed to the compounds of formulae (I), (II) or (III) or their pharmaceutical acceptable salts for use for used in treating colorectal and liver cancers.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

The present invention is directed to compounds and their acceptable pharmaceutical salts, to pharmaceutical compositions comprising them and their use in the manufacture of medicaments for treating diseases. In particular, the compounds may be used for treating cancer, such as colon and liver cancers. Acceptable pharmaceutical salts are selected from suitable pharmaceutically acceptable salts of the compounds of the invention include acid addition salts formed with pharmaceutically acceptable organic or inorganic acids, for example hydrochlorides, hydrobromides, sulphates, alkyl- or arylsulphonates (e.g. methanesulphonates or p-toluenesulphonates), phosphates, acetates, citrates, succinates, tartrates, trifluoroacetates, lactates, fumarates, malates and maleates.

The pharmaceutical compositions according to the present invention may be in a solid form of capsules, or tablets; or may be in a form suitable for topical administration as ointments, creams, lotions, or gels. Alternatively, it may be in the form of drops, syrups, suspensions, injectable powders, or liquid in ampoules.

When present in a liquid form, the active component according to the present invention is dissolved in a solvent or mixture of solvents that are allowed for in vivo use (GRAS). In particular, DMSO, Cyclodextrins, such as α-Cyclodextrin, 2-hydroxypropyl-β-cyclodextrin, 3-hydroxypropyl-β-cyclodextrin, 4-Sulfo-butyl-cyclodextrin solutol, cremophor were used. The compositions may comprise carbohydrates such as, lactose, dextrose, sucrose, trehalose, dextrates.

The effect of the compounds Z522-0249, Z522-0251, Erbitux and E-626-0342 on the growth profile of cancer cells which express Fer was tested. The cells that were tested were: the colon cancer cell lines HT29, HCT 116, RKO, SW620, and SW48 and the liver cancer cell line Hep3B. The effect of each of the three compounds (Z522-0249, Z522-0251 and E-626-0342) on FS11 cells, a non malingnant fibroblastic cell line, was also studied.

EXPERIMANTAL

Biological Studies

Figure 1:
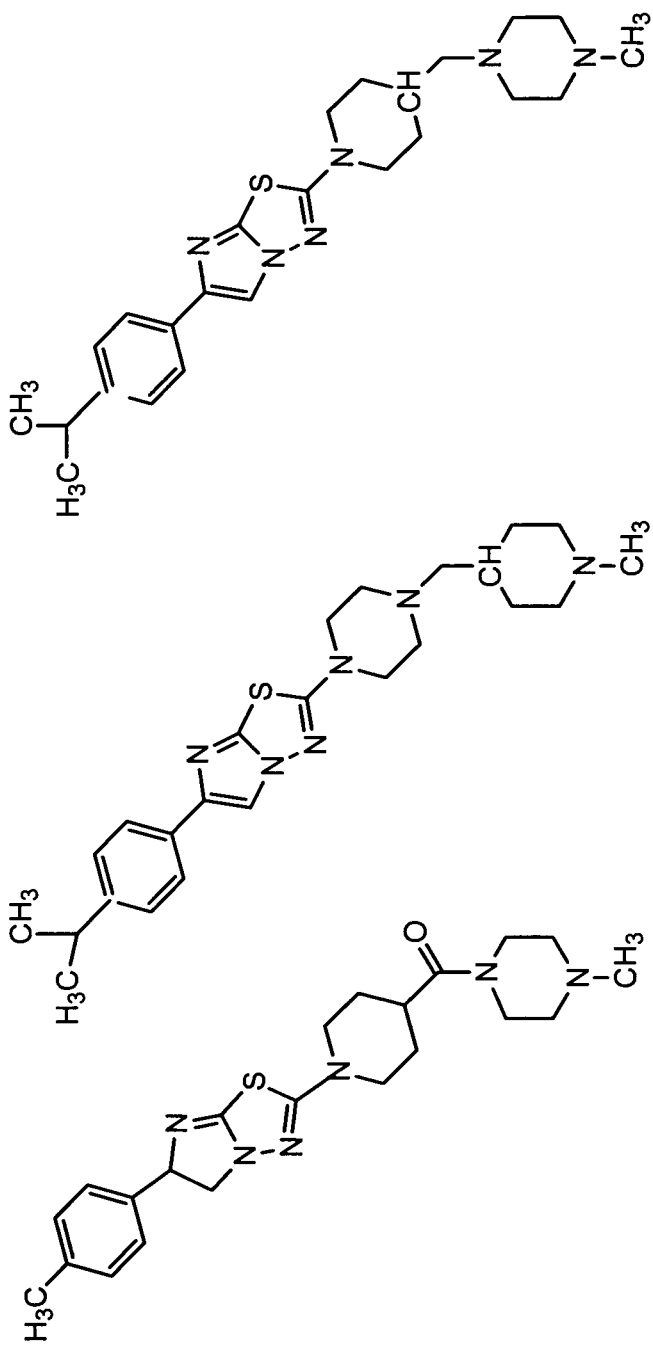
FIG. 1 shows the structural formula of compounds Z522-0249, Z522-0251 (both of the present invention) and E626-0342 (WO2009/019708).
Figure 2:
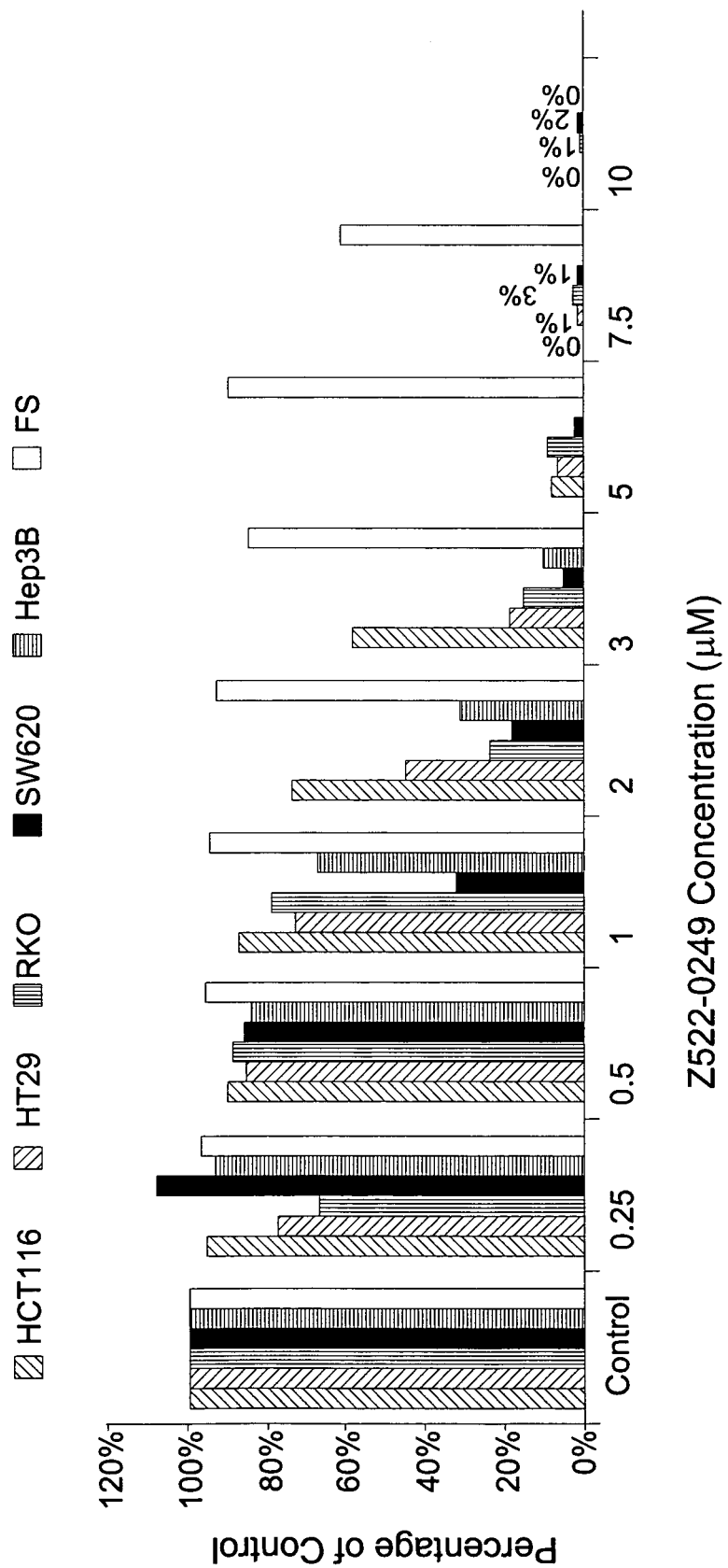
FIG. 2 shows the effect of compound Z522-0249 on the viability of HCT116, HT29, RKO, SW620, Hep3B, FS (normal fibroblasts) and SW48 cells.
Figure 3:
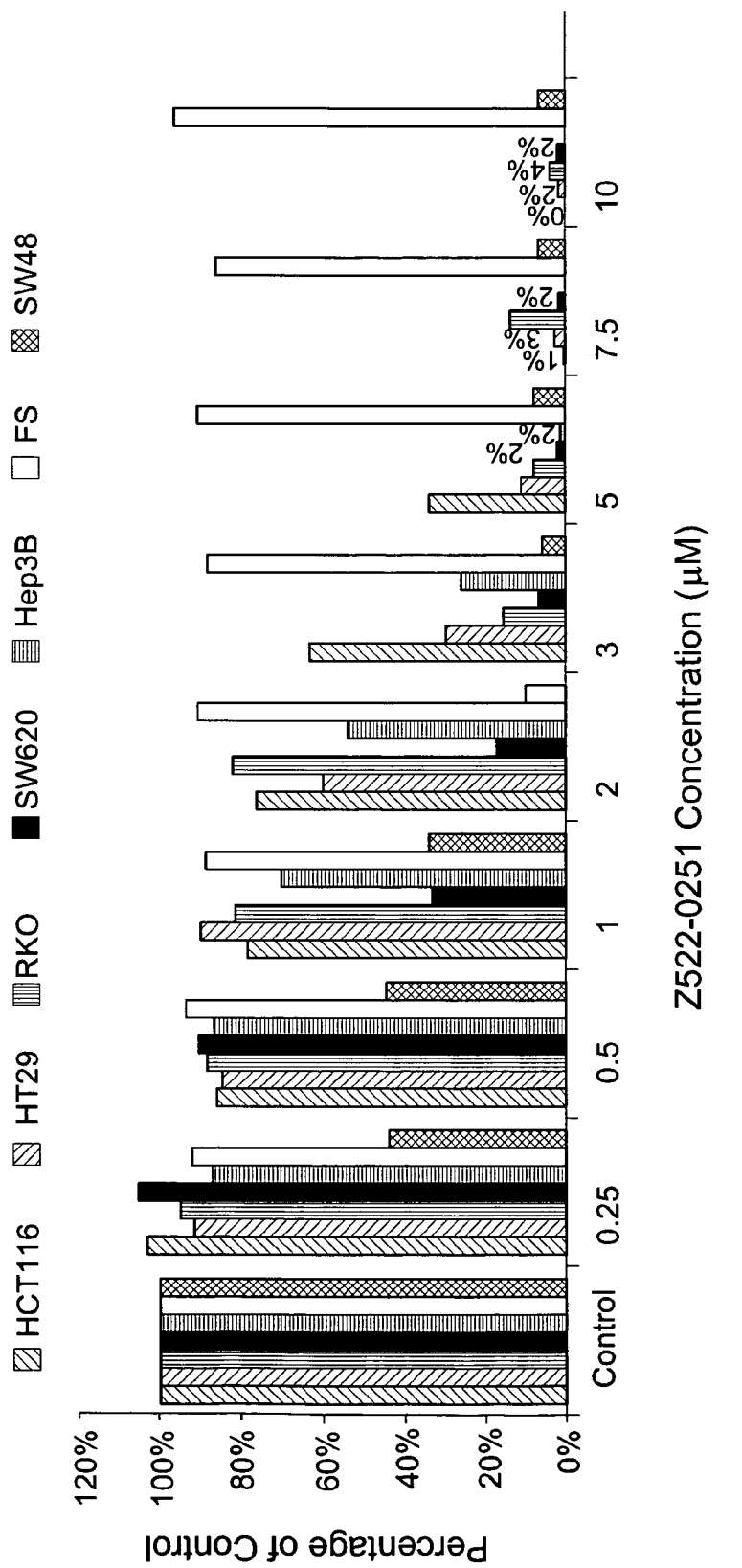
FIG. 3 shows the effect of compound Z522-0251 on the viability of HCT116, HT29, RKO, SW620, Hep3B, FS (normal fibroblasts) and SW48 cells.

Cells were seeded in 96 well microplates and were left to grow untreated overnight. Z522-0249 and Z522-0251 were dissolved in 30 mM HEPES pH=7 and were then added to each well in a dose dependent manner from 0.25 to 10 μM. E626-0342 was dissolved in DMSO and was then added to each well in a dose dependent manner from 0.1 to 5 μM. The concentration of DMSO in each well was 0.4% v/v. Untreated cells and cells subjected to 30 mM HEPEs pH=7 or 0.4% DMSO alone, served as controls. The number of viable cells in each well was determined 48, 72, and 96 hours after compound addition, using the XTT test (Berridge, M. V. et al, 2005). In cases where complete inhibition of cell growth was observed in the presence of one of the three compounds tested at one of the concentrations tested, the IC50 of the compound on that cell line was determined FIGS. 2 and 3 show the effect of compounds Z522-0249 and Z522-0251, resepectively, on the growth of the colorectal cancer cell lines HT29, HCT116, RKO, SW620, and SW48 and the liver cancer cell line Hep3B.

Figure 4:
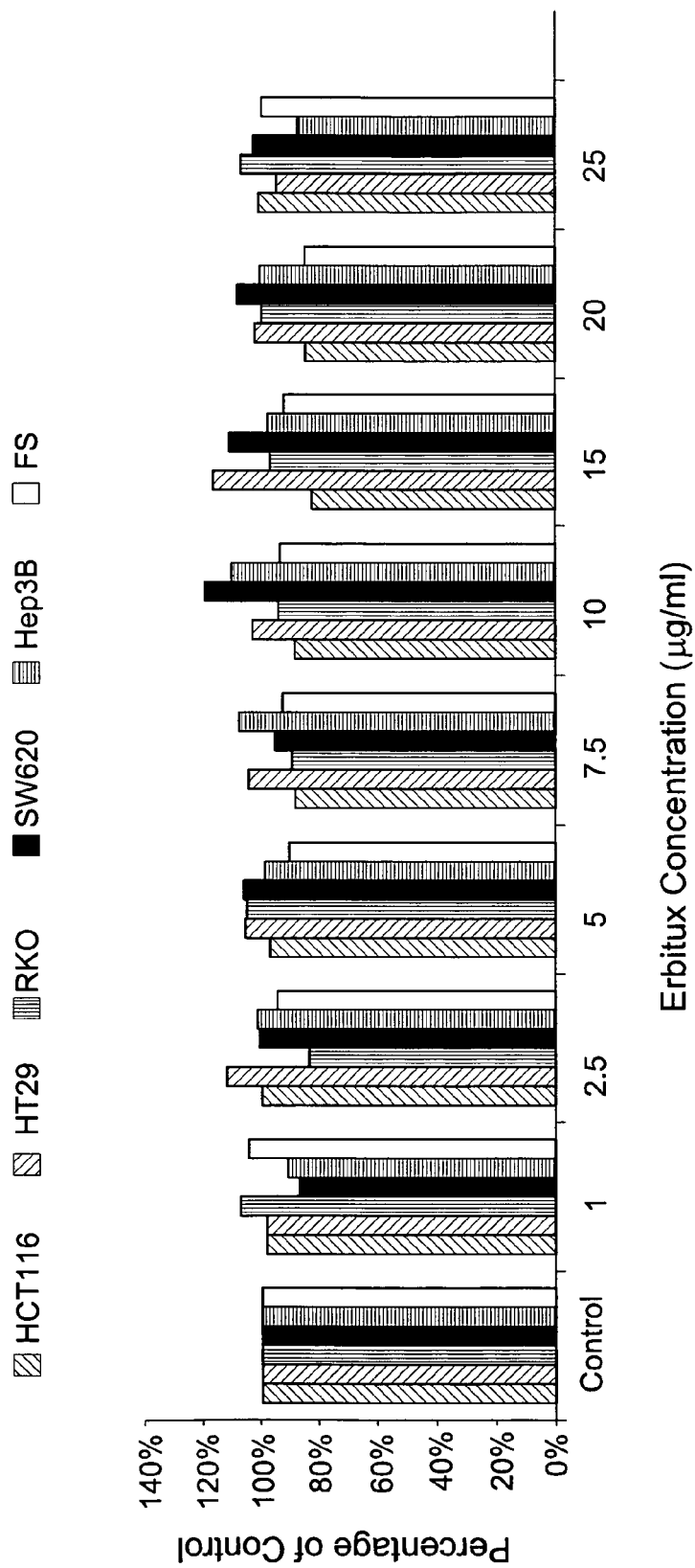
FIG. 4 shows the effect of Erbitux on the viability of HCT116, HT29, RKO, SW620, Hep3B, FS (normal fibroblasts) and SW48 cells.
Figure 5:
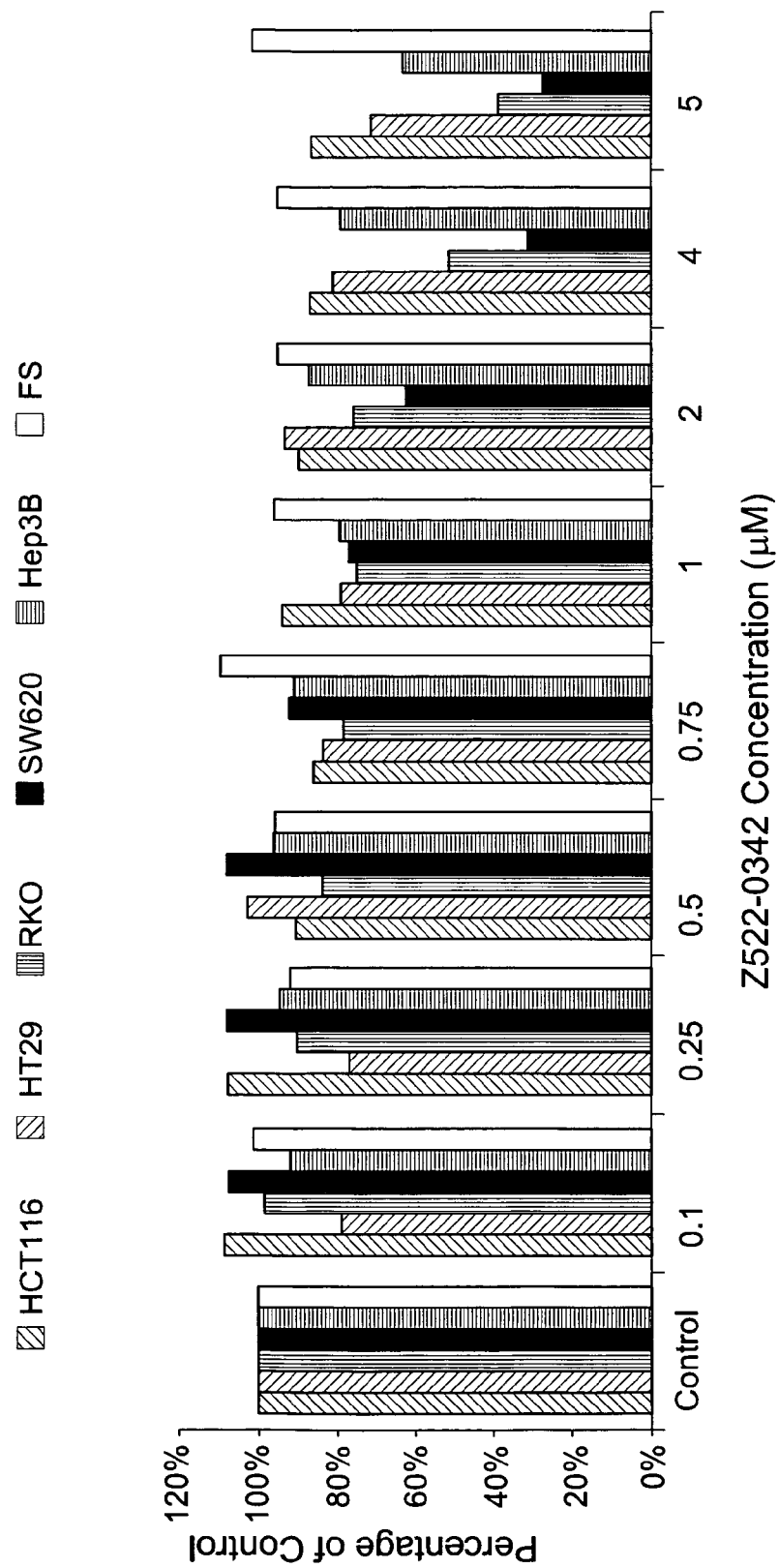
FIG. 5 shows the effect of E626-0342 on the viability of HCT116, HT29, RKO, SW620, Hep3B, FS (normal fibroblasts) and SW48 cells.

FIGS. 4 and 5 show the effect of Erbitux and compound E626-0342, respectively on the growth of the colorectal cancer cell lines HT29, HCT116, RKO, SW620, and SW48 and the liver cancer cell line Hep3B.

EC50 values of the Z522-0249 and Z522-0251 compounds on colon and liver cancer cells are given in Table I below.

TABLE I

EC50 values of the Z522-0249 and Z522-0251
compounds on colon and liver cancer cells

| compound | cell line | | | | | | |
|---|---|---|---|---|---|---|---|
| | HCT116 | HT29 | RKO | SW620 | SW48 | Hep3B | FS |
| Z522-0249 | 3 μM | 2 μM | 1-2 μM | 0.5-1 μM | 0.5-1 μM | 1-2 μM | 10 μM |
| Z522-0251 | 3-4 μM | 2-3 μM | 2-3 μM | 0.5-1 μM | 0.5-1 μM | 1-2 μM | — |

Salts of Z522-0251
Liquid Formulations
A. The compound, Z522-0251 as tartarate salt (0251T), was dissolved in 10% Solutol to a stock solution of 8.5 mM. Next it was diluted with PBS to 0.2 mM 0251T+0.23% Solutol to a solution that was used to prepare several solutions of 0251T in PBS with variable concentrations as follows: 10, 15, 20, 40, 60, 100, 150, and 200 μM. These solutions were used for evaluating the ability of 0251T to affect the viability of several cell lines as follows:

FS, HT29 and SW-620 Cells were seeded in 96 plates–190 μl cells added to each well+10 μl of different concentration of the compound to final concentrations as follows: 0.5, 0.75, 1, 2, 3, 5, 7.5, 10 μM.

As control, SW620 and FS Cells were seeded in 96 plates– 190 μl cells added to each well+10 μl buffer exactly as above but with out the compound.

Cells were grown for 96 hours and their viability tested with XTT kit.

Figure 6:
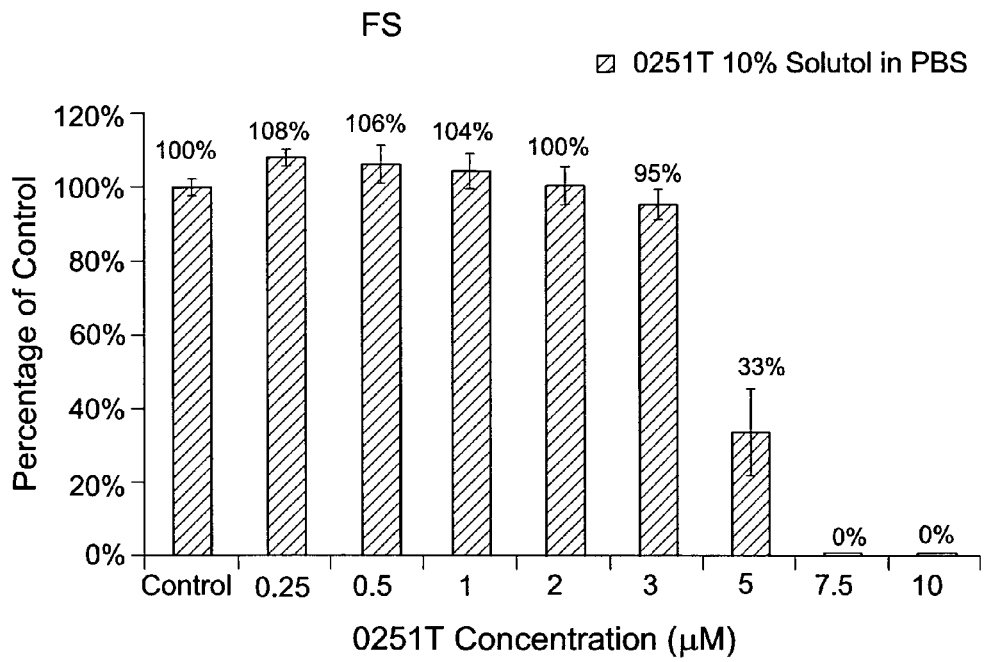
FIG. 6 shows the effect of the tartarate salt of Z522-0251 (0251T) in various concentrations in solutol on the viability of FS cells.
Figure 7:
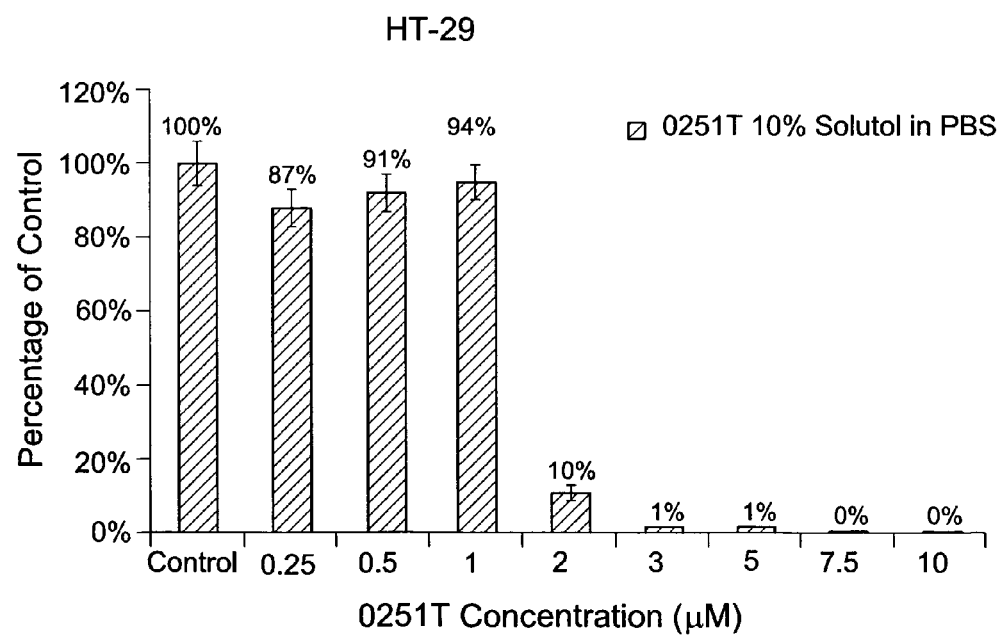
FIG. 7 shows the effect of the tartarate salt of Z522-0251 (0251T) in various concentrations in solutol on the viability of HT-29 cells.
Figure 8:
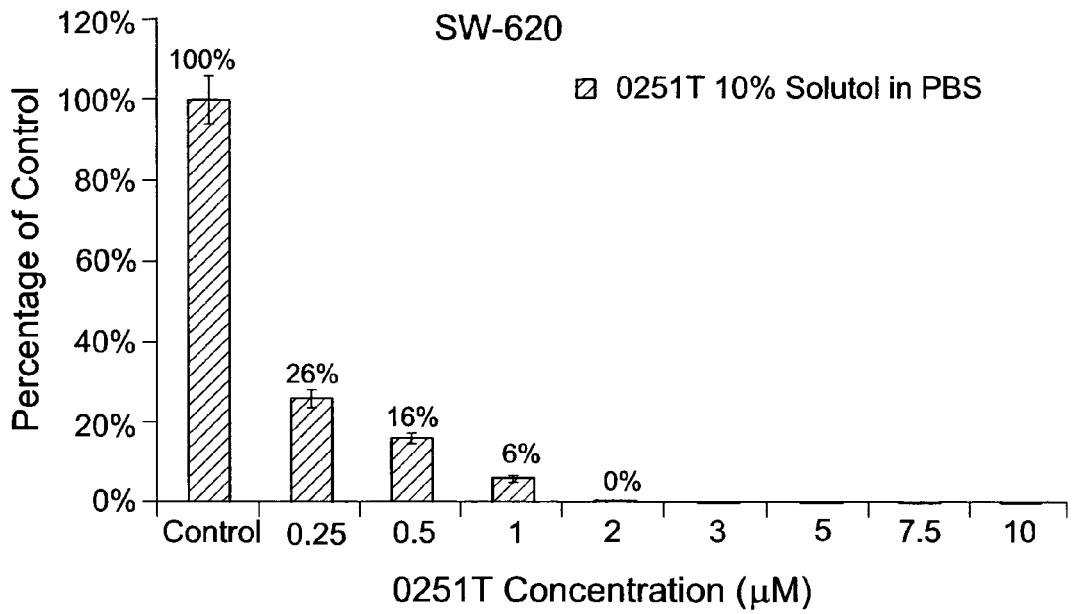
FIG. 8 shows the effect of the tartarate salt of Z522-0251 (0251T) in various concentrations in solutol on the viability of SW-620 cells.

Results for the viability of FS, HT29 and SW-620 Cells in the above concentrations are given in FIGS. 6-8.

B. The compound, Z522-0251 as tartarate salt (0251T), was dissolved in 30% Cremophor to a stock solution of 8.5 mM.

Next it was diluted with PBS to 0.2 mM 0251T+0.72% Cremophor to a solution that was used to prepare several concentrations of the compound in PBS with variable concentrations as follows: 10, 15, 20, 40, 60, 100, 150, and 200 µM. These solutions were used for evaluating the ability of 0251T to affect the viability of several cell lines as follows:

SW620 and FS Cells were seeded in 96 plates–190 µl cells added to each well+10 µl of different concentration of the compound to final concentration as follows: 0.5, 0.75, 1, 2, 3, 5, 7.5, 10 µM.

As control, SW620 and FS Cells were seeded in 96 plates–190 µl cells added to each well+10 µl buffer exactly as above but with out the compound.

Cells were grown for 96 hours and their viability tested with XTT kit.

Figure 9:
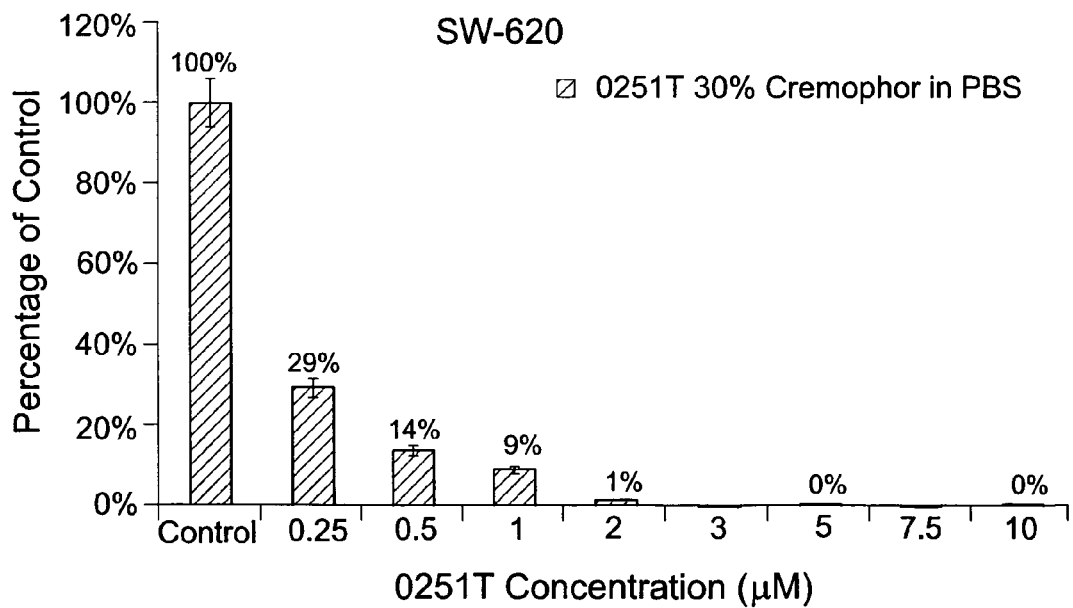
FIG. 9 shows the effect of the tartarate salt of Z522-0251 (0251T) in various concentrations in cremophor on the viability of SW-620 cells.
Figure 10:
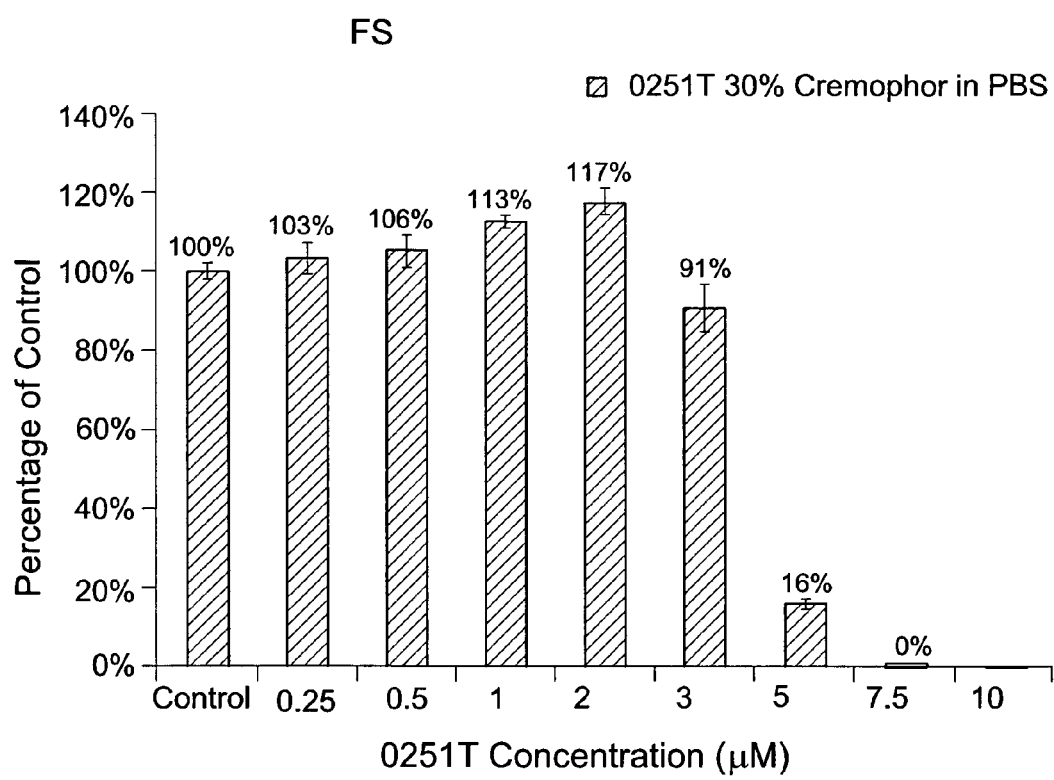
FIG. 10 shows the effect of the tartarate salt of Z522-0251 (0251T) in various concentrations in cremophor on the viability of FS cells.
Figure 11:
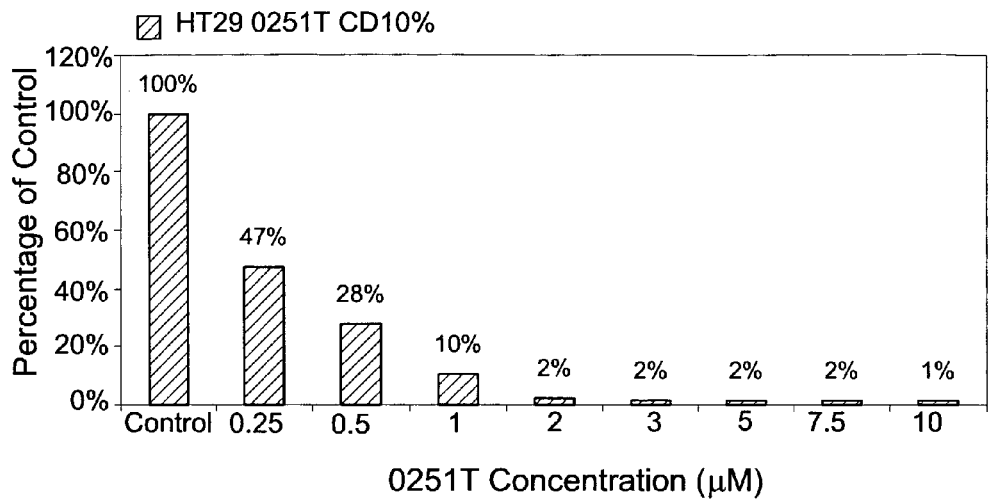
FIG. 11 shows the effect of the tartarate salt of Z522-0251 (0251T) in various concentrations in 2-hydroxypropyl-β-cyclodextrin on the viability of HT-29 cells.
Figure 12:
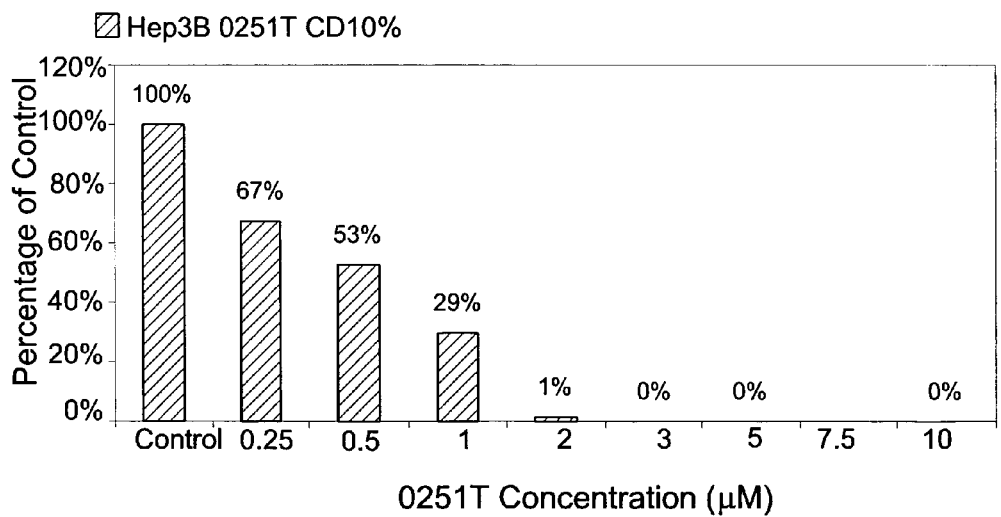
FIG. 12 shows the effect of the tartarate salt of Z522-0251 (0251T) in various concentrations in 2-hydroxypropyl-β-cyclodextrin on the viability of Hep3B cells.
Figure 13:
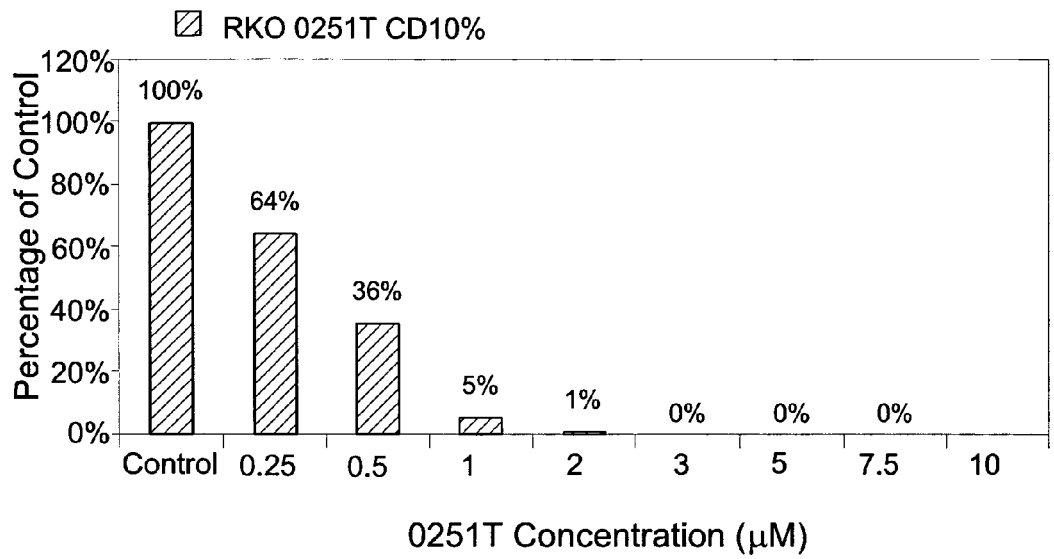
FIG. 13 shows the effect of the tartarate salt of Z522-0251 (0251T) in various concentrations in 2-hydroxypropyl-β-cyclodextrin on the viability of RKO cells.
Figure 14:
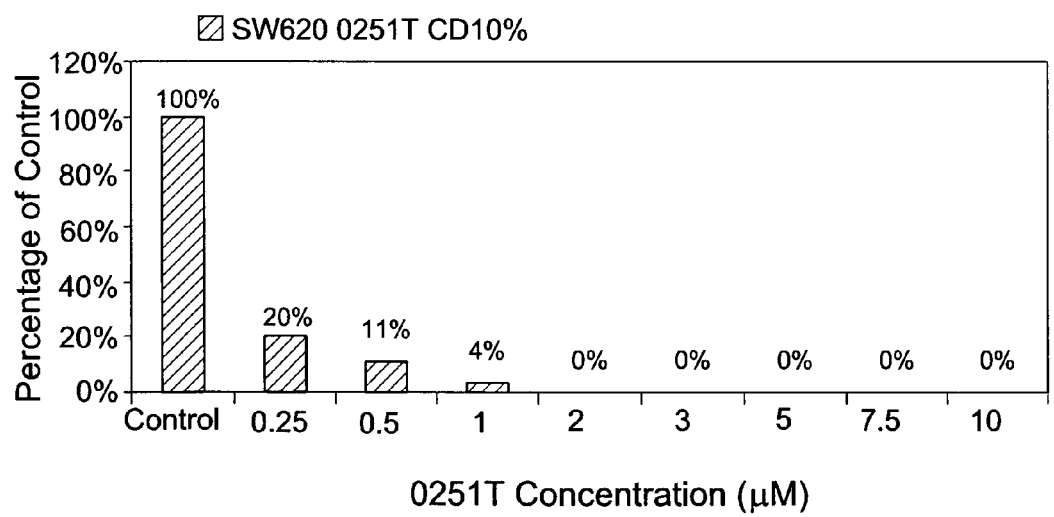
FIG. 14 shows the effect of the tartarate salt of Z522-0251 (0251T) in various concentrations on the viability of SW-620 cells.

Results for the viability of SW-620 and FS Cells in the above concentrations are given in FIGS. 9 and 10.

C. The compound, 0251 as tartarate salt (0251T), was dissolved in 10% 2-hydroxypropyl-β-cyclodextrin to a stock solution of 8.5 mM. Next it was diluted in PBS to 0.2 mM+0.23% 2-hydroxypropyl-β-cyclodextrin. This solution was used to prepare several concentration of the compound in PBS with variable concentrations as follows: 10, 15, 20, 40, 60, 100, 150, and 200 µM. These solutions were used for evaluating the ability of 0251T to affect the viability of several cell lines as follows:

HT29, HEP3B, RKO and SW620 Cells were seeded in 96 plates–190 µl cells added to each well+10 µl of different concentration of the compound to final concentration as follows: 0.5, 0.75, 1, 2, 3, 5, 7.5, 10 µM.

As control, SW620, HT29, HEP3B and RKO Cells were seeded in 96 plates–190 µl cells added to each well+10 µl buffer exactly as above but with out the compound.

Cells were grown for 96 hours and their viability tested with XTT kit.

Results for the viability of HT29, HEP3B, RKO and SW620 Cells in the above concentrations are given in FIGS. 11-14.

Chemical Synthesis

Compounds of formula (II) were prepared according to Scheme 1:

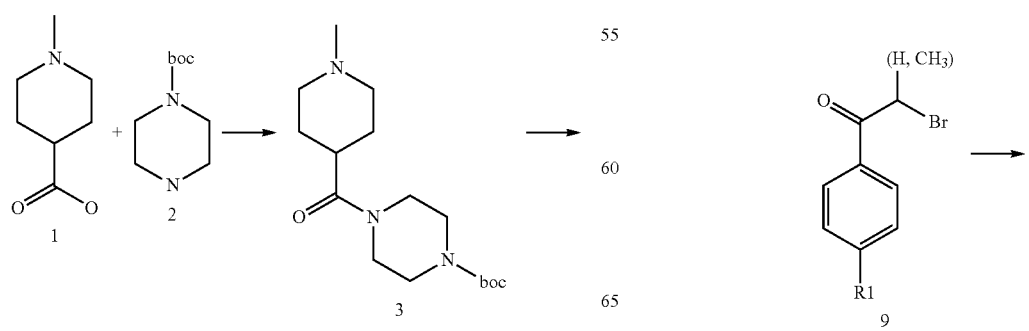

Scheme 1

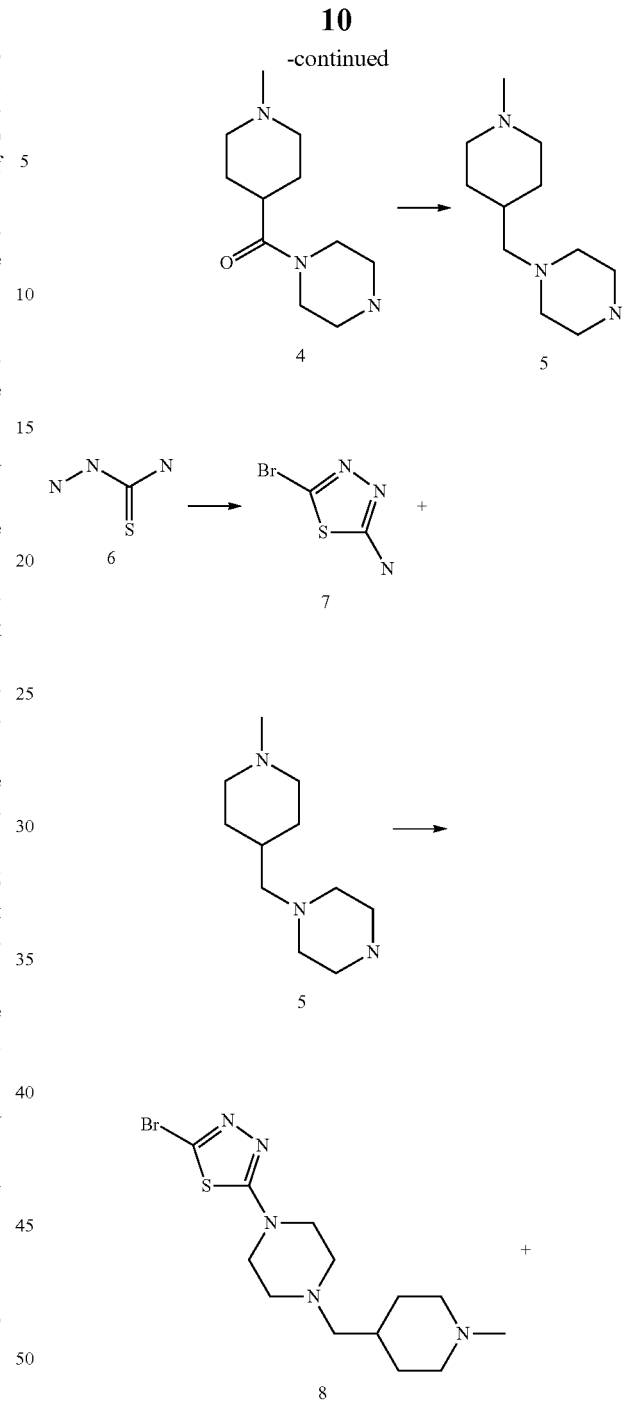

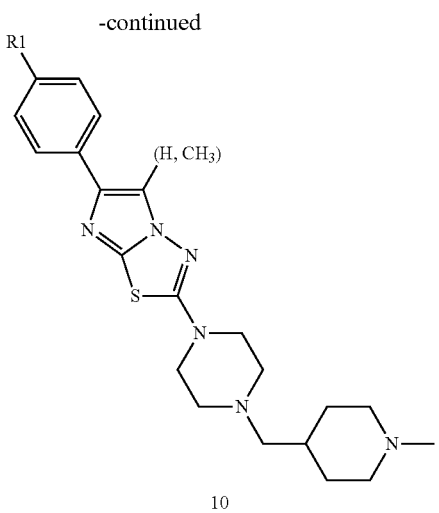

Preparation

Preparation of 3

0.1 mol of 1 was stirred with 0.11 mol of CDI in 200 ml of chloroform at room temperature for 2 hours. Then 2 (0.1 mol) was added and reaction mixture was stirred at room temperature overnight. 200 ml of water were added, after that organic layer was separated and solvent removed under reduced pressure.

Preparation of 4

20 g of 3 was stirred in 200 ml of 1,4-dioxane*HCl at room temperature overnight. Solvent was removed under reduced pressure, residue was diluted with 5% water solution of $Na_2CO_3$ and formed precipitate was filtered off

Preparation of 5

20 mmol of 4 was suspended in 20 ml of diethyl ether. $LiAlH_4$ (100 mmol) was slowly added and reaction mixture was refluxed for 48 hours. Then reaction mixture was cooled down, 4 ml of water were added drop-wise, after that 4 ml of a 10% aqueous solution of NaOH were added. The reaction mixture was then filtered and the solid washed twice with 50 ml of diethyl ether. Ether solutions were combined and solvent was removed under reduced pressure.

Preparation of 7

1 mol of 6 was suspended in 50 ml of 85% water aqueous formic acid and 80 ml of sulfuric acid were carefully added. The reaction mixture was stirred for 3 hours in a boiling water bath and then cooled down. 800 ml of water were added and the reaction mixture was alkalified by water ammonia solution to pH 3.5. Then the reaction mixture was heated to 55° C. and 68.5 ml of $Br_2$ were added drop-wise under liquid layer, while keeping the temperature at 55° C. and pH 3.5. The reaction mixture was stirred at this temperature overnight and after that it was cooled down and alkalified by water ammonia solution to pH 8. Precipitate was formed, filtered off, washed with water and dried.

Preparation of 8

0.1 Mol of 6 was dissolved in 200 ml of ethanol. 0.1 Mol of 5 and 0.11 mol of triethylamine were added and the reaction mixture was refluxed for 4 hours. Then the solvent was removed under reduced pressure and the residue was washed with water, filtered off and dried.

Preparation of 10

0.2 mmol of 8 was dissolved in 2 ml of DMF and 0.2 mmol of 9 was added. Reaction mixture was stirred at 100° C. overnight. Then the reaction mixture was diluted with 50 ml of water, extracted with 10 ml of chloroform, the solvent was removed under reduced pressure and the product was isolated by column chromatography (chloroform:methanol—20:1 as an eluent) or by HPLC.

Using the appropriate starting materials, the following compounds were further synthesized.

| ID | structure | UPAC name | Identification |
|---|---|---|---|
| Z522-0152 | 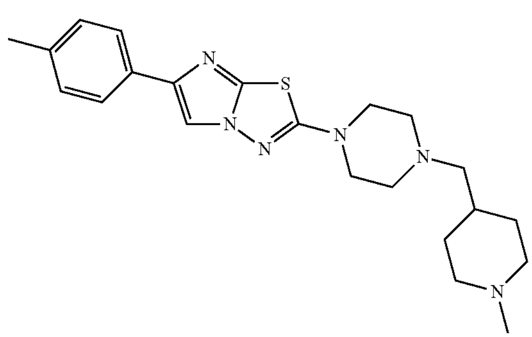 [SMILES: Cc1ccc(-c2cn3nc(N4CCN(CC5CCN(C)CC5)CC4)sc3n2)cc1] | 6-(4-methylphenyl)-2-{4-[(1-methylpiperidin-4-yl)methyl]piperazin-1-yl}imidazo[2,1-b][1,3,4]thiadiazole | LCMS: M + 1 = 411 |

-continued

| ID | structure | UPAC name | Identification |
|---|---|---|---|
| Z522-0153 | 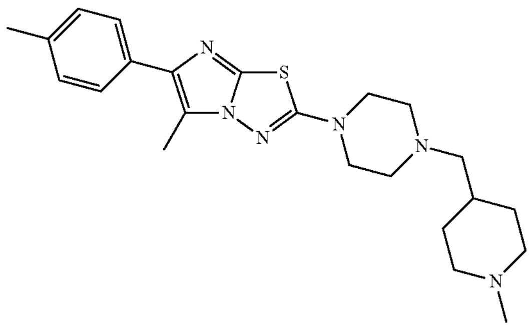 [SMILES: Cc1ccc(-c2nc3sc(N4CCN(CC5CCN(C)CC5)CC4)nn3c2C)cc1] | 5-methyl-6-(4-methylphenyl)-2-{4-[(1-methylpiperidin-4-yl)methyl]piperazin-1-yl}imidazo[2,1-b][1,3,4]thiadiazole | LCMS: M + 1 = 425 |
| Z522-0245 | 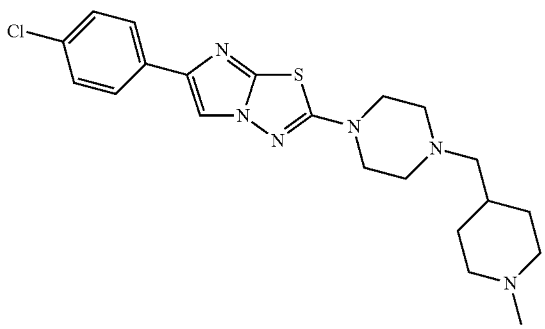 [SMILES: CN1CCC(CN2CCN(c3nn4cc(-c5ccc(Cl)cc5)nc4s3)CC2)CC1] | 6-(4-chlorophenyl)-2-{4-[(1-methylpiperidin-4-yl)methyl]piperazin-1-yl}imidazo[2,1-b][1,3,4]thiadiazole | LCMS: M + 1 = 432 |
| Z522-0246 | 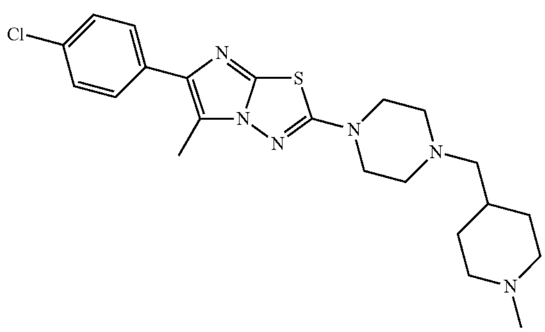 | 6-(4-chlorophenyl)-5-methyl-2-{4-[(1-methylpiperidin-4-yl)methyl]piperazin-1-yl}imidazo[2,1-b][1,3,4]thiadiazole | LCMS: M + 1 = 446 |
| Z522-0249 | 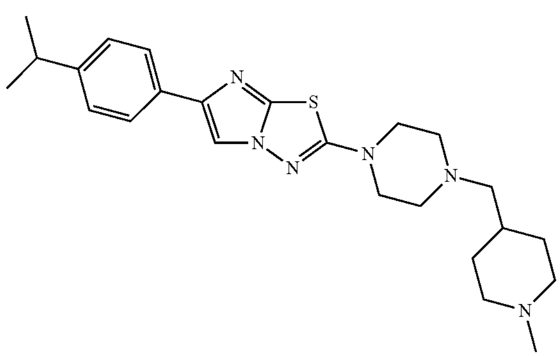 [SMILES: CC(C)c1ccc(-c2cn3nc(N4CCN(CC5CCN(C)CC5)CC4)sc3n2)cc1] | 6-(4-isopropylphenyl)-2-{4-[(1-methylpiperidin-4-yl)methyl]piperazin-1-yl}imidazo[2,1-b][1,3,4]thiadiazole | LCMS: M + 1 = 439 |
| Z522-0250 | 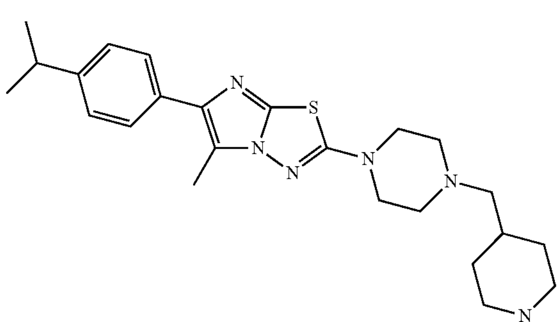 | 6-(4-isopropylphenyl)-5-methyl-2-{4-[(1-methylpiperidin-4-yl)methyl]piperazin-1-yl}imidazo[2,1-b][1,3,4]thiadiazole | LCMS: M + 1 = 453 |

Preparation of compounds of formula (III) was done according to schemes 2 and 3:

Scheme 2

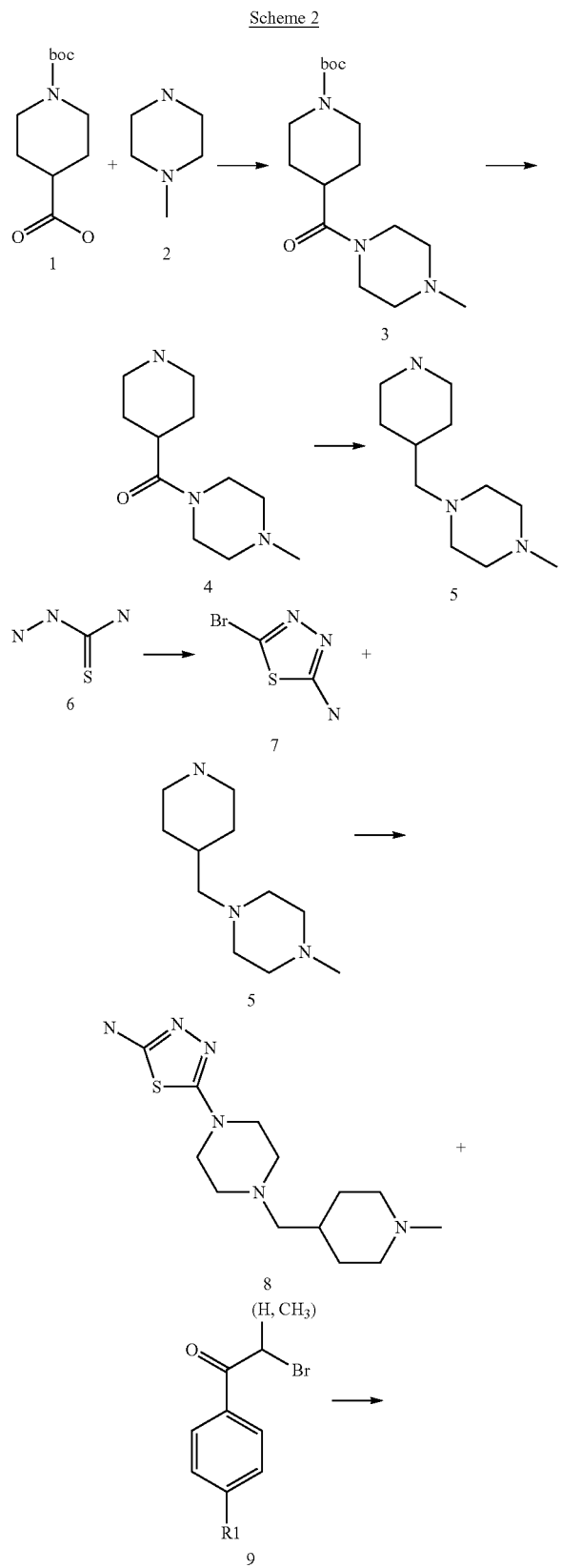

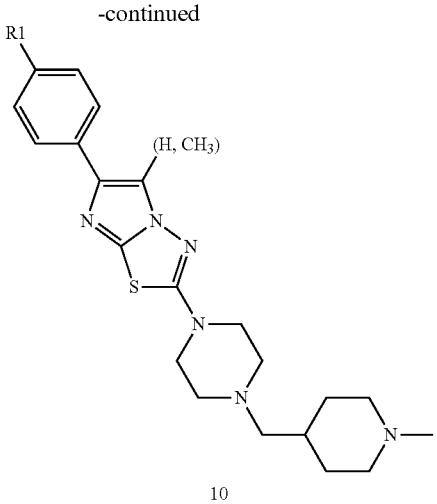

Preparation

Preparation of 3

0.1 mol of 1 was stirred with 0.11 mol of CDI in 200 ml of chloroform at room temperature for 2 hours. Then 2 (0.1 mol) was added and reaction mixture was stirred at room temperature overnight. 200 ml of water were added, after that organic layer was separated and solvent removed under reduced pressure.

Preparation of 4

20 g of 3 was stirred in 200 ml of 1,4-dioxane*HCl at room temperature overnight. Solvent was removed under reduced pressure, residue was diluted with 5% water solution of $Na_2CO_3$ and formed precipitate was filtered off.

Preparation of 5

20 mmol of 4 was suspended in 20 ml of diethyl ether. $LiAlH_4$ (100 mmol) was slowly added and reaction mixture was refluxed for 48 hours. Then reaction mixture was cooled down, 4 ml of water were added dropwise, after then 4 ml of 10% water solution of NaOH were added. Then reaction mixture was filtered and solid washed twice with 50 ml of diethyl ether. Ether solutions were combined and solvent removed under reduced pressure.

Preparation of 7

1 mol of 6 was suspended in 50 ml of 85% water formic acid and 80 ml of sulfuric acid were carefully added. Reaction mixture was stirred for 3 hours on boiling water bath and then cooled down. 800 ml of water were added and reaction mixture was alkalified by water ammonia solution to ph 3.5. Then reaction mixture was heated to 55° C. and 68.5 ml of $Br_2$ were added dropwise under liquid layer, keeping on temperature 55° C. and pH 3.5. Reaction mixture was stirred at this temperature overnight and after that it was cooled down and alkalified by water ammonia solution to ph 8. Precipitate was formed, filtered off, washed by water and dried.

Preparation of 8

0.1 mol of 6 was dissolved in 200 ml of ethanol. 0.1 mol of 5 and 0.11 mol of triethylamine were added and reaction mixture was refluxed for 4 hours. Then solvent was removed under reduced pressure and residue was washed by water, filtered off and dried.

Preparation of 10

0.2 mmol of 8 was dissolved in 2 ml of DMF and 0.2 mmol of 9 was added. Reaction mixture was stirred at 100° C. overnight. Then reaction mixture was diluted with 50 ml of water, extracted with 10 ml of chloroform, solvent was removed under reduced pressure and product was isolated by column chromatography (chloroform:methanol—20:1 as an eluent) or by HPLC.

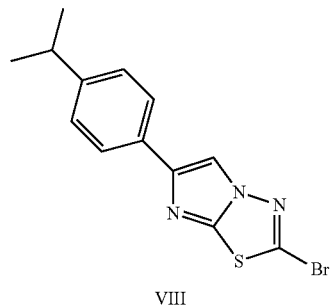

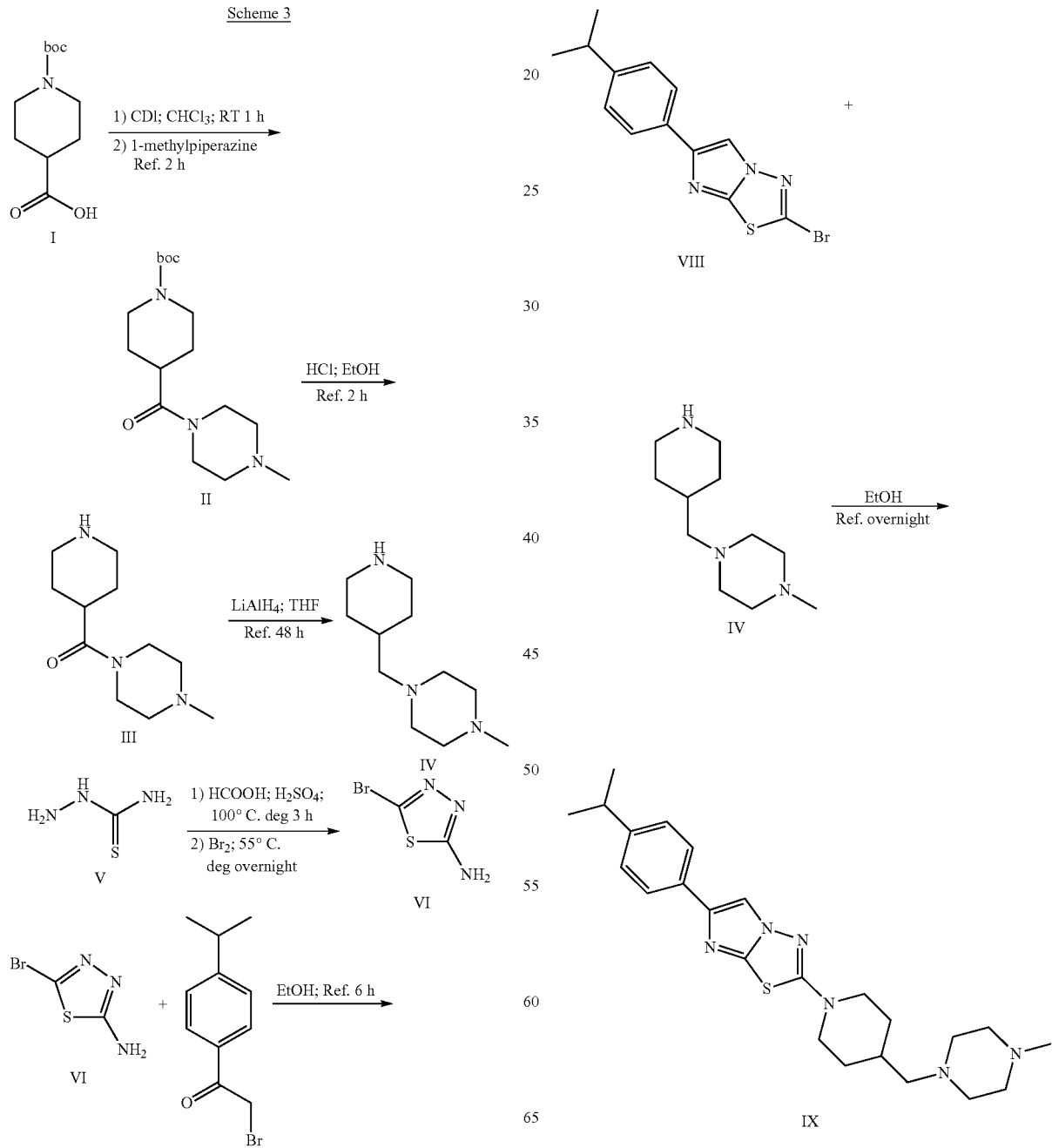

Experimental

¹H NMR spectra were acquired on a Bruker DPX-400 spectrometer (400.40 MHz) using solvents (DMSO-$d_6$ or $CDCl_3$) as internal standards. The chemical shifts are given as δ (ppm). LCMS spectra were recorded with a PE SCIEX API 165 (150) mass-spectrometer (HPLC: Intertsil 3 mkm ODS-3 50×20 mm; eluent: A=$H_2O$+TFA (0.05%), B=$CH_3CN$+TFA (0.05%); 0.01 min—controller start, 4.00 min—pump B—95.0%, 5.50 min—pump B—95.0%, 5.90 min—pump B—5.0%, 6.00 min—controller stop).

tert-butyl 4-[(4-methylpiperazin-1-yl)carbonyl]piperidine-1-carboxylate II 218 mmol (50.00 g) of I was stirred with 218 mmol (35.36 g) of CDI in 500 ml of chloroform at room temperature for 1 hour. Then 1-methylpiperazine 218 mmol (21.84 g) was added and reaction mixture was stirred under reflux for 2 hours. When reaction mass was cooled down to RT, 200 ml of water was added, phases were separated, organic phase was washed with water (2×100 ml), after that combined organic layers were dried under anhydrous $Na_2SO_4$ and solvent was removed under reduced pressure to provide title compound 66.55 g (98%) as colorless oil.

1-methyl-4-(piperidin-4-ylcarbonyl)piperazine bis hydrochloride III 217 mmol (67.57 g) of II was dissolved in 400 ml of EtOH and 36 ml of concentrated hydrochloric acid was added. Reaction mass was stirred under reflux for 2 hours. When colled down, formed precipitate was removed by filtration, washed with EtOH and air dried to provide III as white solid 36.40 g (59%).

1-methyl-4-(piperidin-4-ylmethyl)piperazine IV $LiAlH_4$ 412.3 mmol (15.649 g) was suspended in 450 ml of absolute THF, when III 126.9 mmol (36.06 g) was slowly added and reaction mixture was refluxed for 48 hours. Then reaction mixture was cooled down, 16 ml of water was added dropwise, after then 16 ml of 15% water solution of NaOH was added and finally 48 ml of water was added. Then reaction mixture was filtered and solid was washed twice with 250 ml of THF. Solvent was removed under reduced pressure to provide title compound 17.77 g (71%) as colorless oil.

5-bromo-1,3,4-thiadiazol-2-amine VI 1 mol of V was suspended in 50 ml of 85% water formic acid and 80 ml of sulfuric acid were carefully added. Reaction mixture was stirred for 3 hours on boiling water bath and then cooled down. 800 ml of water were added and reaction mixture was alkalified by water ammonia solution to ph 3.5. Then reaction mixture was heated to 55° C. and 68.5 ml of $Br_2$ were added dropwise under liquid layer, keeping on temperature 55° C. and ph 3.5. Reaction mixture was stirred at this temperature overnight and after that it was cooled down and basified by water ammonia solution to ph 8. Precipitate which was formed was filtered off, washed by water and dried to provide title compound 153.02 g (85%).

2-bromo-6-(4-isopropylphenyl)imidazo[2,1-b][1,3,4]thiadiazole VIII 38.88 mmol (7.000 g) of VI was suspended in 70 ml of absolute EtOH, when VII 38.88 mmol (9.376 g) was added and reaction mixture was heated under reflux for 6 hours. When solvent was removed under reduced pressure, residue was dissolved in water, pH was adjusted to 9-10 by NaOH solution, water phase was extracted by $CHCl_3$ (3×50 ml), organic phase was dried under $Na_2SO_4$ and concentrated under reduced pressure. The oily residue was purified by column chromatography on silica (eluent=hexane:ethylacetate 18:1) to provide the product VIII (3.250 g, 26%) as white solid.

6-(4-isopropylphenyl)-2-{4-[(4-methylpiperazin-1-yl)methyl]piperidin-1-yl}imidazo[2,1-b][1,3,4]thiadiazole IX 23.03 mmol (7.420 g) of VIII was suspended in 110 ml of absolute EtOH, when 50.66 mmol (5.126 g) of triethylamine and 23.03 mmol (4.544 g) of IV was added and reaction mixture was heated under reflux overnight. When volatile substances were removed under reduced pressure. The solid residue was purified by column chromatography on silica (eluent=$CHCl_3$:MeOH 19:1) to provide the product IX (3.961 g, 39%) as white solid.

Using the appropriate starting materials the following compounds were further synthesized:

| ID | structure | UPAC name | Identification |
|---|---|---|---|
| Z522-0154 | 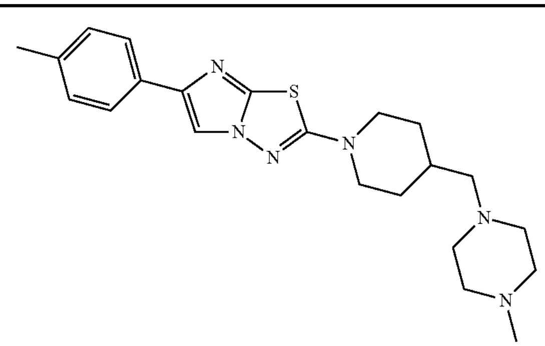 | 6-(4-methylphenyl)-2-{4-[(4-methylpiperazin-1-yl)methyl]-piperidin-1-yl}imidazo[2,1-b][1,3,4]thiadiazole | LCMS: M + 1 = 410 |

-continued

| ID | structure | UPAC name | Identification |
|---|---|---|---|
| Z522-0156 | 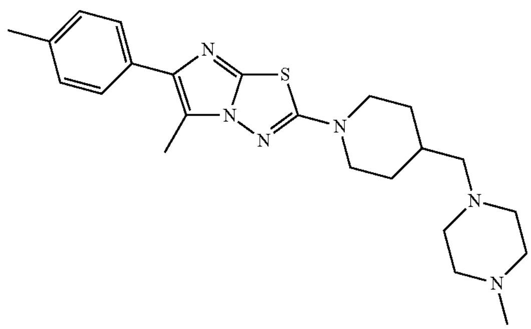 [SMILES: Cc1ccc(-c2nc3sc(N4CCC(CN5CCN(C)CC5)CC4)nn3c2C)cc1] | 5-methyl-6-(4-methylphenyl)-2-{4-[(4-methylpiperazin-1-yl)methyl]-piperidin-1-yl}imidazo[2,1-b][1,3,4]thiadiazole | LCMS: M + 1 = 425 |
| Z522-0247 | 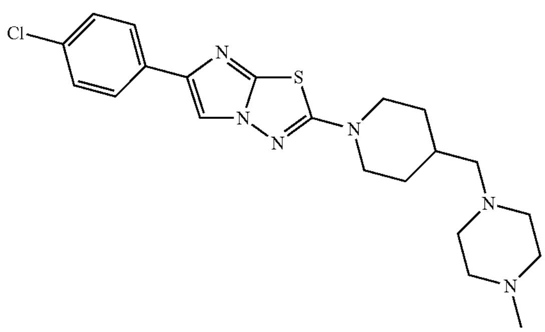 [SMILES: CN1CCN(CC2CCN(c3nn4cc(-c5ccc(Cl)cc5)nc4s3)CC2)CC1] | 6-(4-chlorophenyl)-2-{4-[(4-methylpiperazin-1-yl)methyl]-piperidin-1-yl}imidazo[2,1-b][1,3,4]thiadiazole | LCMS: M + 1 = 432 |
| Z522-0248 | 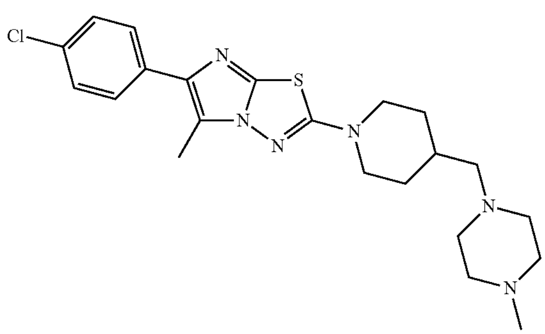 [SMILES: Cc1c(-c2ccc(Cl)cc2)nc2sc(N3CCC(CN4CCN(C)CC4)CC3)nn12] | 6-(4-chlorophenyl)-5-methyl-2-{4-[(4-methylpiperazin-1-yl)methyl]piperidin-1-yl}imidazo[2,1-b][1,3,4]thiadiazole | LCMS: M + 1 = 446 |
| Z522-0251 | 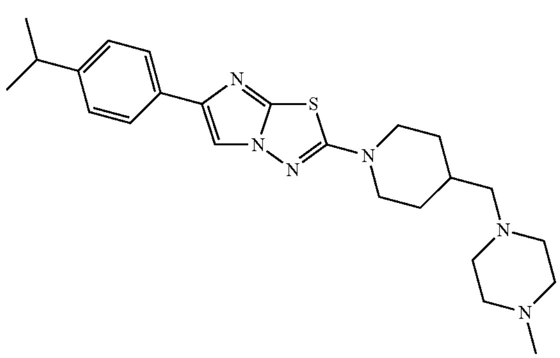 [SMILES: CC(C)c1ccc(-c2cn3nc(N4CCC(CN5CCN(C)CC5)CC4)sc3n2)cc1] | 6-(4-isopropyl-phenyl)-2-{4-[(4-methyl-piperazin-1-yl)methyl]piperidin-1-yl}imidazo[2,1-b][1,3,4]thiadiazole | LCMS: M + 1 = 439 |

-continued

| ID | structure | UPAC name | Identification |
|---|---|---|---|
| Z522-0254 | 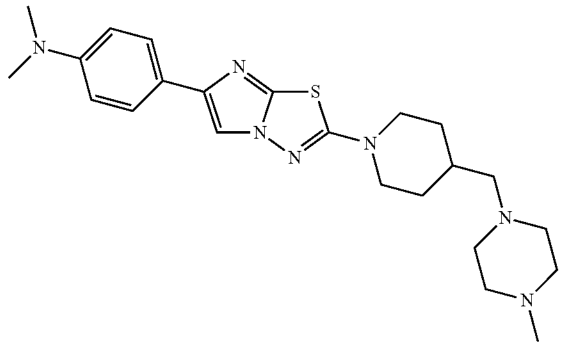 [SMILES: CN1CCN(CC2CCN(c3nn4cc(-c5ccc(N(C)C)cc5)nc4s3)CC2)CC1] | N,N-dimethyl-4-(2-{4-[(4-methyl-piperazin-1-yl)methyl]piperidin-1-yl}imidazo[2,1-b][1,3,4]thiadiazol-6-yl)aniline | LCMS: M + 1 = 440 |
| Z522-0255 | 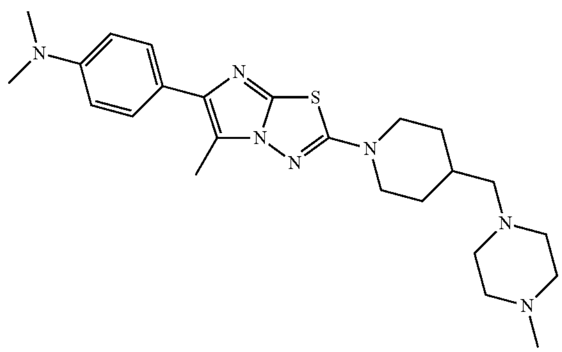 [SMILES: Cc1c(-c2ccc(N(C)C)cc2)nc2sc(N3CCC(CN4CCN(C)CC4)CC3)nn12] | N,N-dimethyl-4-(5-methyl-2-{4-[(4-methylpiperazin-1-yl)methyl]piperidin-1-yl}imidazo[2,1-b][1,3,4]thiadiazol-6-yl)aniline | LCMS: M + 1 = 454 |
| Z522-0256 | 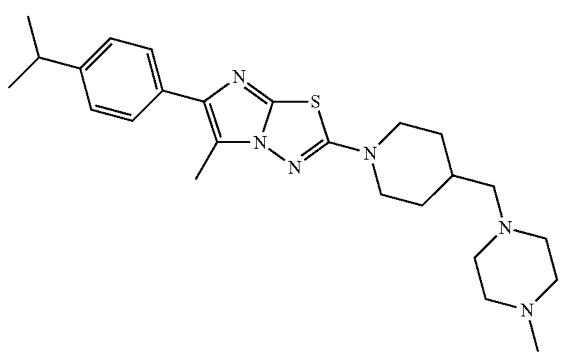 [SMILES: Cc1c(-c2ccc(C(C)C)cc2)nc2sc(N3CCC(CN4CCN(C)CC4)CC3)nn12] | 6-(4-isopropylphenyl)-5-methyl-2-{4-[(4-methylpiperazin-1-yl)methyl]piperidin-1-yl}imidazo[2,1-b][1,3,4]thiadiazole | LCMS: M + 1 = 453 |

The invention claimed is:

1. A compound of formula (I) or a pharmaceutically acceptable salt thereof:

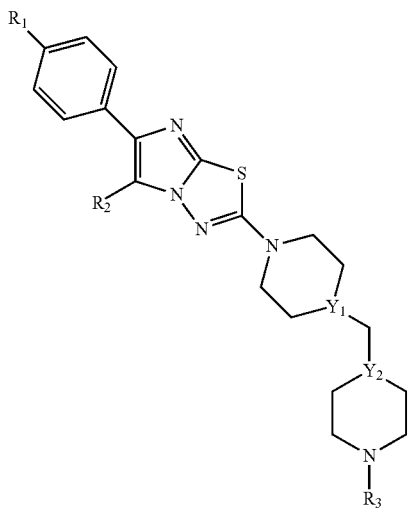

(I)

wherein $R_1$, $R_2$ and $R_3$ are each independently selected from hydrogen, halogen, $C_{1-6}$alkyl, $C_{2-6}$alkenyl, N—$(C_{1-6}$alkyl$)_2$, and N—$(C_{2-6}$alkenyl$)_2$, the $C_{1-6}$alkyl and $C_{2-6}$alkenyl being straight or branched; and $Y_1$ and $Y_2$ are selected from N and CH where one of $Y_1$ and $Y_2$ is N and the other is CH.

2. The compound according to claim 1 wherein $R_1$ is methyl, ethyl, propyl, isopropyl, N-(isopropyl)$_2$, butyl, sec.-butyl, tert.-butyl, N-(butyl)$_2$, HN-(sec.butyl)$_2$, N-tert.-butyl, F, Cl, Br, or I; $R_2$ is hydrogen, methyl, ethyl, propyl, isopropyl, or butyl; and $R_3$ is hydrogen, methyl, ethyl, propyl, isopropyl, or butyl.

3. A compound of formulae (II) or (III) or a pharmaceutically acceptable salt thereof:

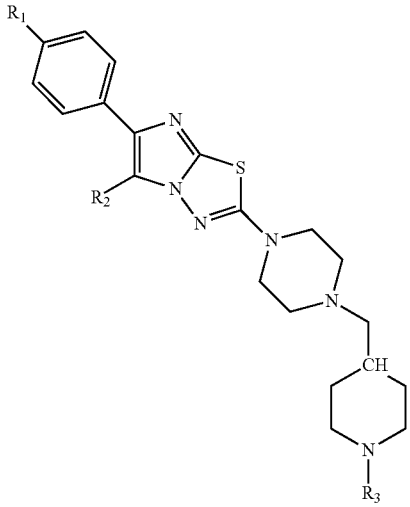

(II)

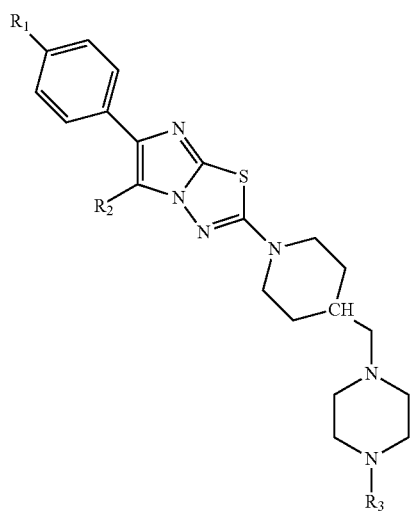

(III)

wherein $R_1$, $R_2$ and $R_3$ are each independently selected from hydrogen, halogen, $C_{1-6}$alkyl, $C_{2-6}$alkenyl, N—$(C_{1-6}$alkyl$)_2$, and N—$(C_{2-6}$alkenyl$)_2$ the $C_{1-6}$alkyl and $C_{2-6}$alkenyl being straight or branched.

4. The compound of formula (II) or (III) according to claim 3:
wherein $R_1$ is hydrogen, methyl, ethyl, propyl, isopropyl, N-(isopropyl)$_2$, butyl, sec.-butyl, tert.-butyl, N-(CH$_3$)$_2$, N-(butyl)$_2$, N-(sec.butyl)2, N-(tert.-butyl)$_2$, F, Cl, Br, or I; $R_2$ is hydrogen, methyl, ethyl, propyl, isopropyl, or butyl; and $R_3$ is hydrogen, methyl, ethyl, propyl, isopropyl, or butyl.

5. A method for treating cancer in a subject comprising administering to the subject a therapeutically effective amount of a compound according to claim 1.

6. A pharmaceutical composition comprising a compound according to claim 1 and one or more excipients.

7. The method according to claim 5 wherein the cancer is colorectal or liver cancer.

8. A process for the preparation of a compound of formula (II) according to claim 3, comprising

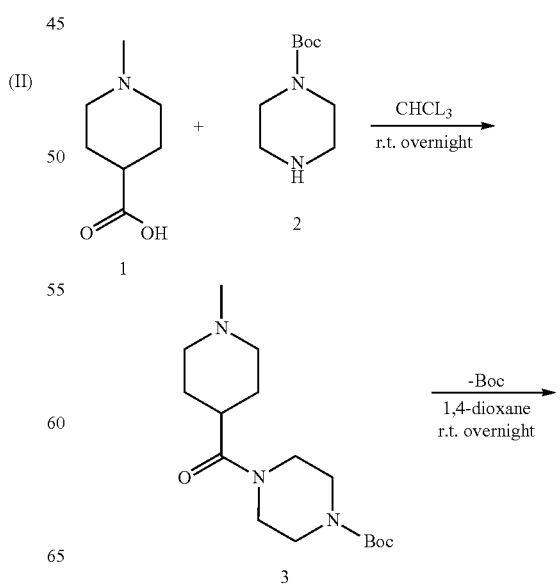

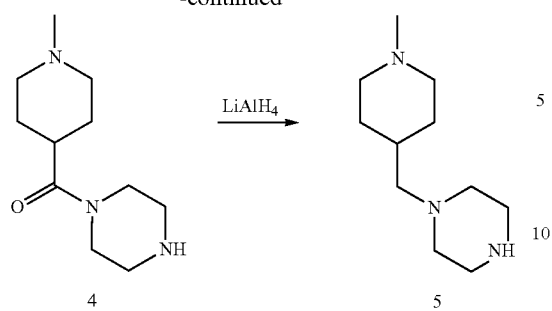
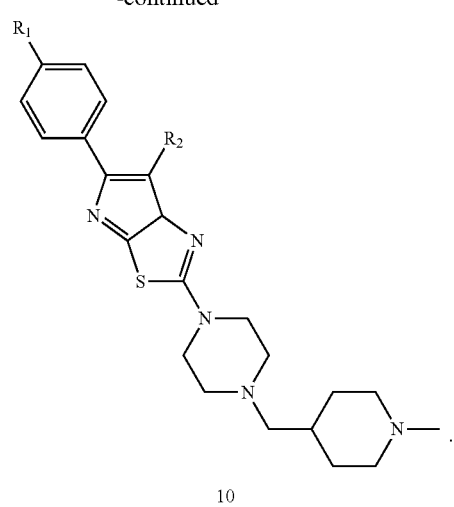
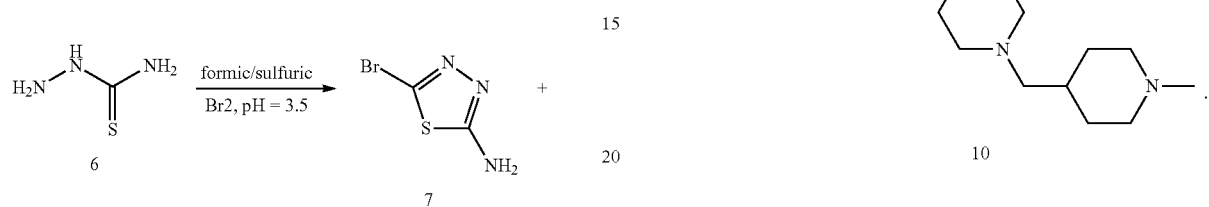
9. A process for the preparation of a compound of formula (III) according to claim 3 comprising
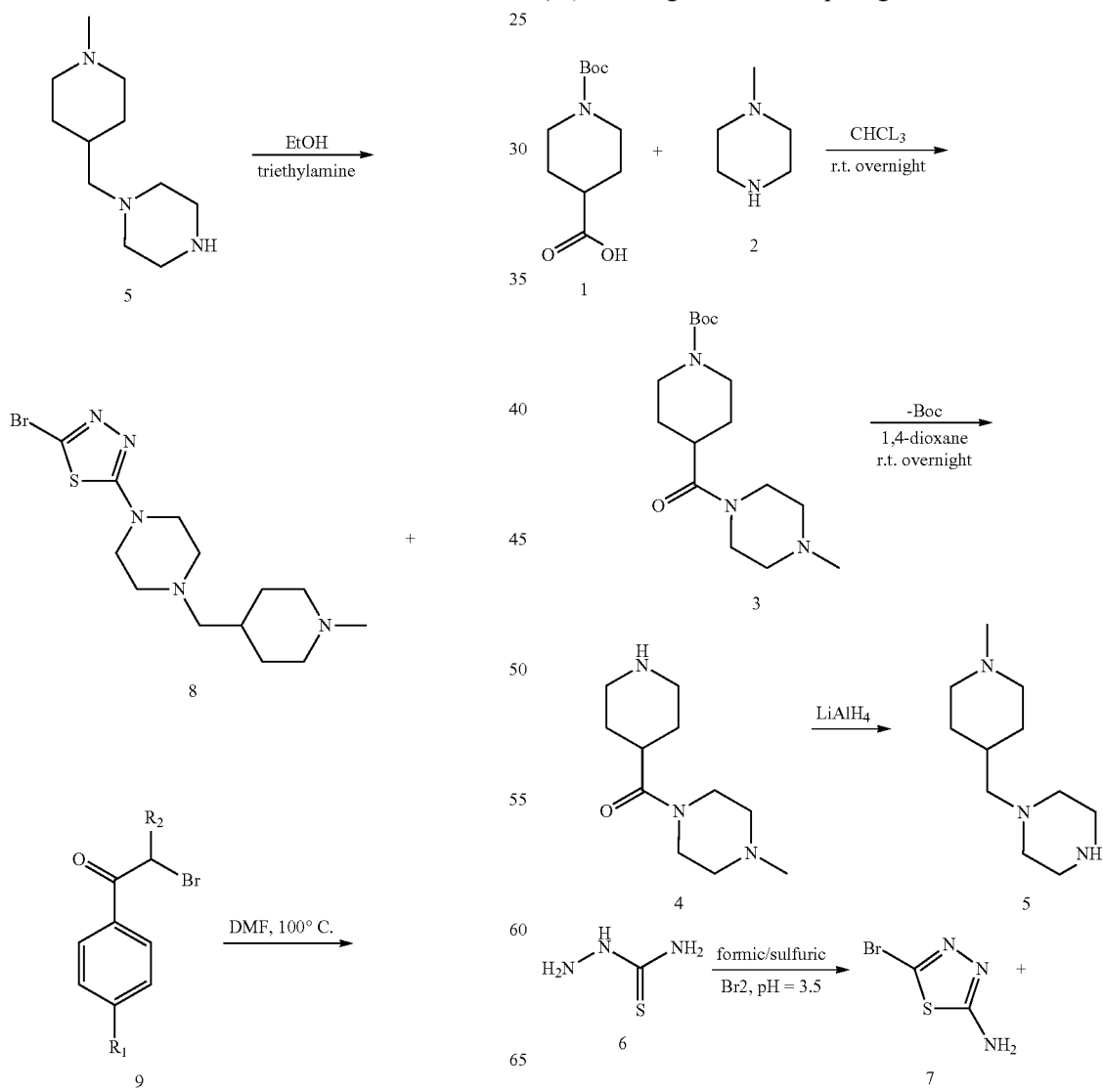

-continued
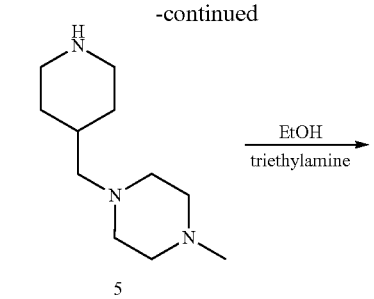
5
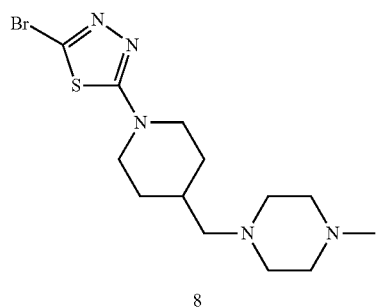
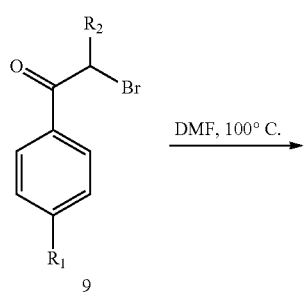
9
-continued
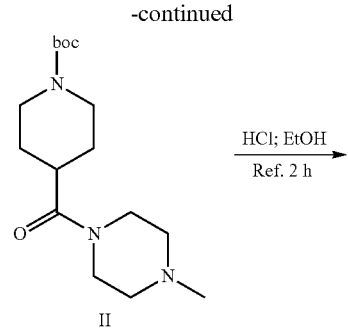
II
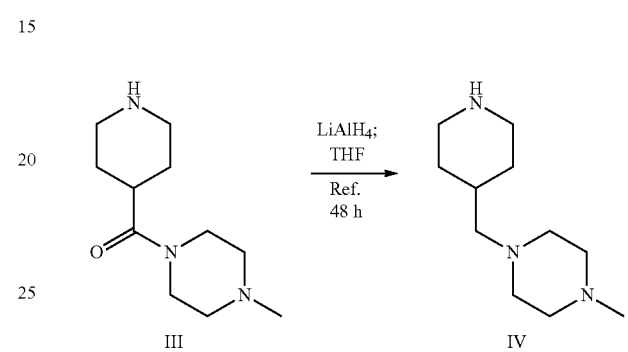
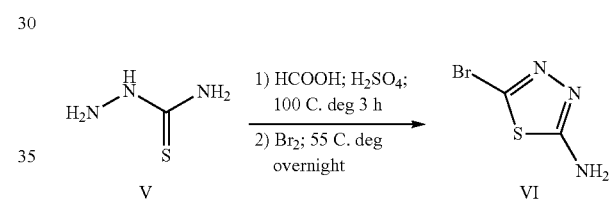
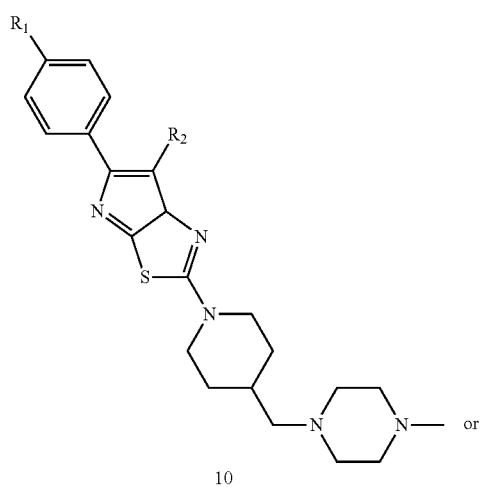
10
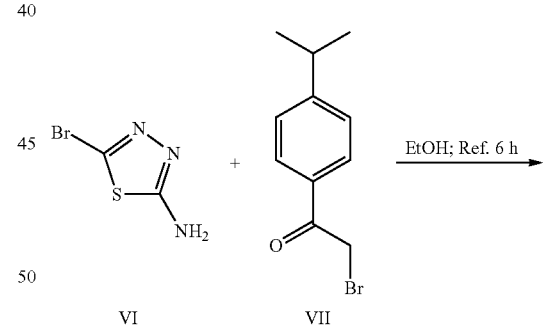
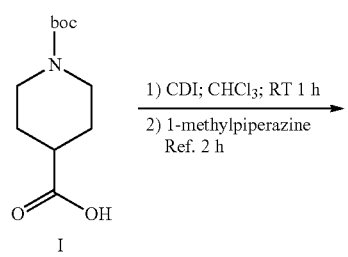
I
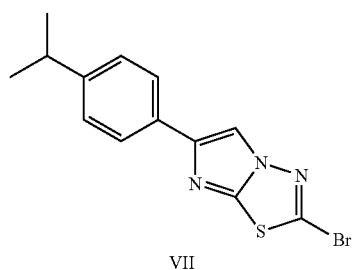
VII -continued
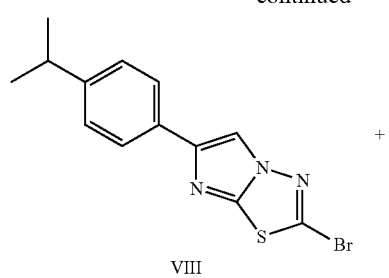
VIII
+
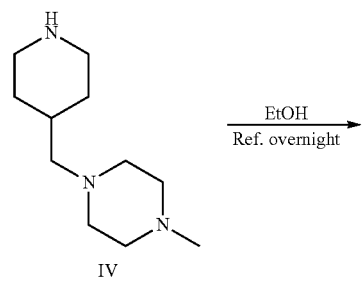
IV
→ EtOH, Ref. overnight
-continued
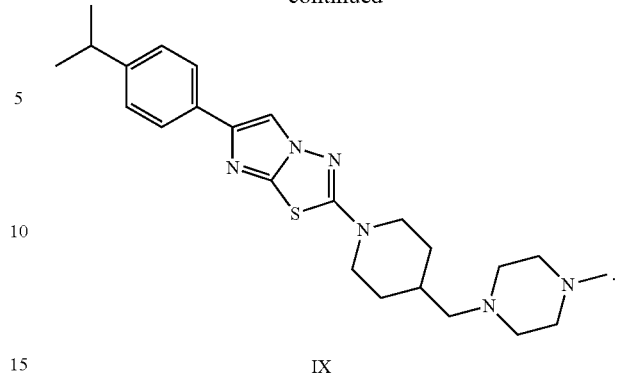
IX
10. The method of claim 5, wherein the cancer is colon cancer.
11. The method of claim 10, wherein the compound is N,N-dimethyl-4-(2-{4-[(1-methylpiperidin-4-yl)methyl]piperazin-1-yl}imidazo[2,1-b][1,3,4]thiadiazol-6-yl)aniline (compound Z522-0252).
* * * * *